US00RE42208E

(19) United States
(12) Reissued Patent
Truncale et al.

(10) Patent Number: US RE42,208 E
(45) Date of Reissued Patent: Mar. 8, 2011

(54) GLUE FOR CARTILAGE REPAIR

(75) Inventors: Katherine Gomes Truncale, Hillsborough, NJ (US); Arthur A. Gertzman, Flemington, NJ (US); Moon Hae Sunwoo, Old Tappan, NJ (US); William W. Tomford, Belmont, MA (US)

(73) Assignee: Musculoskeletal Transplant Foundation, Edison, NJ (US)

(21) Appl. No.: 12/147,042

(22) Filed: Jun. 26, 2008

Related U.S. Patent Documents

Reissue of:
(64) Patent No.: 7,067,123
Issued: Jun. 27, 2006
Appl. No.: 10/424,765
Filed: Apr. 29, 2003

(51) Int. Cl.
*A61K 35/32* (2006.01)

(52) U.S. Cl. ..... 424/93.7; 424/548
(58) Field of Classification Search ..... None
See application file for complete search history.

(56) References Cited

U.S. PATENT DOCUMENTS

| | | | | |
|---|---|---|---|---|
| 3,400,199 | A | 9/1968 | Balassa | |
| 3,551,560 | A | 12/1970 | Theile | |
| 3,772,432 | A * | 11/1973 | Balassa | 424/548 |
| 3,867,728 | A | 2/1975 | Stubstad et al. | |
| 3,966,908 | A | 6/1976 | Balassa | |
| 4,060,081 | A | 11/1977 | Yannas et al. | |
| 4,172,128 | A | 10/1979 | Thiele et al. | |
| 4,201,845 | A | 5/1980 | Feder et al. | |
| 4,296,100 | A | 10/1981 | Franco | |
| 4,378,347 | A | 3/1983 | Franco | |
| 4,394,370 | A | 7/1983 | Jefferies | |
| 4,400,833 | A | 8/1983 | Kurland | |
| 4,442,655 | A | 4/1984 | Stroetmann | |

(Continued)

FOREIGN PATENT DOCUMENTS

| | | |
|---|---|---|
| EP | 0517030 A2 | 12/1992 |
| EP | 0522569 A1 | 1/1993 |
| EP | 0762903 B1 | 6/1995 |

(Continued)

OTHER PUBLICATIONS (No Author)"Lyophilization" TechnoBusinesss–Solutions. (No publication date). Retrieved Jul. 1, 2009 from URL: <http://www.technobusiness–solutions.com/ article–lyophilization1.html> 10 pages.*

(Continued)

*Primary Examiner*—Allison M Ford
(74) *Attorney, Agent, or Firm*—Greenberg Traurig, LLP

(57) ABSTRACT

The invention is directed toward a sterile cartilage defect implant material comprising milled lyophilized allograft cartilage pieces ranging from 0.01 mm to 1.0 mm in size in a bioabsorbable carrier taken from a group consisting of sodium hyaluronate, hyaluronic acid and its derivatives, gelatin, collagen, chitosan, alginate, buffered PBS, Dextran or polymers with allogenic chondrocytes or bone marrow cells in an amount exceeding the natural occurrence of same in hyaline cartilage and adding a cell growth additive.

78 Claims, 1 Drawing Sheet

U.S. PATENT DOCUMENTS

| | | | | |
|---|---|---|---|---|
| 4,458,678 | A | | 7/1984 | Yannas et al. |
| 4,479,271 | A | | 10/1984 | Bolesky et al. |
| 4,501,269 | A | | 2/1985 | Bagby |
| 4,505,266 | A | | 3/1985 | Yannas et al. |
| 4,600,574 | A | | 7/1986 | Lindner et al. |
| 4,627,853 | A | | 12/1986 | Campbell et al. |
| 4,642,120 | A | | 2/1987 | Nevo et al. |
| 4,656,137 | A | | 4/1987 | Balassa |
| 4,681,763 | A | | 7/1987 | Nathanson et al. |
| 4,683,195 | A | | 7/1987 | Mullis et al. |
| 4,683,202 | A | | 7/1987 | Mullis |
| 4,757,017 | A | | 7/1988 | Cheung |
| 4,776,173 | A | | 10/1988 | Kamarei et al. |
| 4,776,853 | A | | 10/1988 | Klement et al. |
| 4,795,467 | A | | 1/1989 | Piez et al. |
| 4,801,299 | A | | 1/1989 | Brendel et al. |
| 4,837,379 | A | | 6/1989 | Weinberg |
| 4,846,835 | A | | 7/1989 | Grande |
| 4,880,429 | A | | 11/1989 | Stone |
| 4,902,508 | A | | 2/1990 | Badylak et al. |
| 4,904,259 | A | | 2/1990 | Itay |
| 4,932,973 | A | | 6/1990 | Gendler |
| 4,950,296 | A | | 8/1990 | McIntyre |
| 4,950,483 | A | | 8/1990 | Ksander et al. |
| 4,955,911 | A | | 9/1990 | Frey et al. |
| 4,963,146 | A | | 10/1990 | Li |
| 4,965,188 | A | | 10/1990 | Mullis et al. |
| 4,971,954 | A | | 11/1990 | Brodsky et al. |
| 4,976,738 | A | | 12/1990 | Frey et al. |
| 4,978,355 | A | | 12/1990 | Frey et al. |
| 4,994,084 | A | | 2/1991 | Brennan |
| 4,994,559 | A | | 2/1991 | Moscatelli et al. |
| 5,002,583 | A | | 3/1991 | Pitaru et al. |
| 5,007,934 | A | | 4/1991 | Stone |
| 5,041,138 | A | | 8/1991 | Vacanti et al. |
| 5,053,049 | A | | 10/1991 | Campbell |
| 5,053,050 | A | | 10/1991 | Itay |
| 5,067,964 | A | | 11/1991 | Richmond et al. |
| 5,073,373 | A | | 12/1991 | O'Leary et al. |
| 5,084,051 | A | | 1/1992 | Tormala et al. |
| 5,118,512 | A | | 6/1992 | O'Leary |
| 5,152,791 | A | | 10/1992 | Hakamatsuka et al. |
| 5,155,214 | A | | 10/1992 | Baird et al. |
| 5,191,067 | A | | 3/1993 | Lappi et al. |
| 5,195,892 | A | | 3/1993 | Gershberg |
| 5,206,023 | A | | 4/1993 | Hunziker |
| 5,236,456 | A | | 8/1993 | O'Leary et al. |
| 5,256,140 | A | | 10/1993 | Fallick |
| 5,260,420 | A | | 11/1993 | Burnouf-Radosevich et al. |
| 5,266,476 | A | | 11/1993 | Sussman et al. |
| 5,270,300 | A | | 12/1993 | Hunziker |
| 5,275,826 | A | | 1/1994 | Badylak et al. |
| 5,284,155 | A | * | 2/1994 | Treadwell et al. ..... 600/562 |
| 5,290,558 | A | | 3/1994 | O'Leary et al. |
| 5,298,254 | A | | 3/1994 | Prewett et al. |
| 5,302,702 | A | | 4/1994 | Seddon et al. |
| 5,306,304 | A | | 4/1994 | Gendler |
| 5,306,311 | A | | 4/1994 | Stone et al. |
| 5,310,883 | A | | 5/1994 | Seddon et al. |
| 5,314,476 | A | | 5/1994 | Prewett et al. |
| 5,326,357 | A | | 7/1994 | Kandel |
| 5,329,846 | A | | 7/1994 | Bonutti |
| 5,336,616 | A | | 8/1994 | Livesey et al. |
| 5,338,772 | A | | 8/1994 | Bauer et al. |
| 5,352,463 | A | | 10/1994 | Badylak et al. |
| 5,354,557 | A | | 10/1994 | Oppermann et al. |
| 5,356,629 | A | | 10/1994 | Sander et al. |
| 5,368,858 | A | | 11/1994 | Hunziker |
| 5,380,328 | A | | 1/1995 | Morgan |
| 5,411,885 | A | | 5/1995 | Marx |
| 5,425,769 | A | | 6/1995 | Snyders, Jr. |
| 5,439,684 | A | | 8/1995 | Prewett et al. |
| 5,439,818 | A | | 8/1995 | Fiddes et al. |
| 5,443,950 | A | | 8/1995 | Naughton et al. |
| 5,464,439 | A | | 11/1995 | Gendler |
| 5,466,462 | A | | 11/1995 | Rosenthal et al. |
| 5,491,220 | A | | 2/1996 | Seddon et al. |
| 5,496,722 | A | | 3/1996 | Goodwin et al. |
| 5,507,813 | A | | 4/1996 | Dowd et al. |
| 5,512,460 | A | | 4/1996 | Nauro et al. |
| 5,513,662 | A | | 5/1996 | Morse et al. |
| 5,516,532 | A | | 5/1996 | Atala et al. |
| 5,556,430 | A | | 9/1996 | Gendler |
| 5,569,272 | A | | 10/1996 | Reed et al. |
| 5,571,895 | A | | 11/1996 | Kurokawa et al. |
| 5,576,288 | A | | 11/1996 | Lappi et al. |
| 5,604,293 | A | | 2/1997 | Fiddes et al. |
| 5,607,474 | A | | 3/1997 | Athanasiou et al. |
| 5,614,496 | A | | 3/1997 | Dunstan et al. |
| 5,618,925 | A | | 4/1997 | Dupont et al. |
| 5,622,928 | A | | 4/1997 | Naruo et al. |
| 5,624,463 | A | | 4/1997 | Stone et al. |
| 5,631,011 | A | | 5/1997 | Wadstrom |
| 5,632,745 | A | | 5/1997 | Schwartz |
| 5,656,598 | A | | 8/1997 | Dunstan et al. |
| 5,662,710 | A | | 9/1997 | Bonutti |
| 5,679,637 | A | | 10/1997 | Lappi et al. |
| 5,695,998 | A | | 12/1997 | Badylak et al. |
| 5,700,476 | A | | 12/1997 | Rosenthal et al. |
| 5,700,774 | A | | 12/1997 | Hattersley et al. |
| 5,707,962 | A | | 1/1998 | Chen et al. |
| 5,713,374 | A | | 2/1998 | Pachence et al. |
| 5,716,413 | A | | 2/1998 | Walter et al. |
| 5,723,331 | A | | 3/1998 | Tubo et al. |
| 5,736,372 | A | | 4/1998 | Vacanti et al. |
| 5,749,874 | A | | 5/1998 | Schwartz |
| 5,759,190 | A | | 6/1998 | Vibe-Hansen et al. |
| 5,769,899 | A | | 6/1998 | Schwartz et al. |
| 5,770,417 | A | | 6/1998 | Vacanti et al. |
| 5,782,835 | A | | 7/1998 | Hart et al. |
| 5,782,915 | A | | 7/1998 | Stone |
| 5,786,217 | A | | 7/1998 | Tubo et al. |
| 5,800,537 | A | | 9/1998 | Bell |
| 5,814,084 | A | | 9/1998 | Grivas et al. |
| 5,842,477 | A | * | 12/1998 | Naughton et al. ..... 128/898 |
| 5,846,931 | A | | 12/1998 | Hattersley et al. |
| 5,853,746 | A | | 12/1998 | Hunziker |
| 5,855,620 | A | | 1/1999 | Bishopric et al. |
| 5,859,208 | A | | 1/1999 | Fiddes et al. |
| 5,863,296 | A | | 1/1999 | Orton |
| 5,863,297 | A | | 1/1999 | Walter et al. |
| 5,866,415 | A | | 2/1999 | Villeneuve |
| 5,876,452 | A | | 3/1999 | Athanasiou et al. |
| 5,888,219 | A | | 3/1999 | Bonutti |
| 5,893,888 | A | | 4/1999 | Bell |
| 5,899,936 | A | | 5/1999 | Goldstein |
| 5,904,716 | A | | 5/1999 | Gendler |
| 5,906,827 | A | | 5/1999 | Khouri et al. |
| 5,910,315 | A | | 6/1999 | Stevenson et al. |
| 5,916,265 | A | | 6/1999 | Hu |
| 5,948,429 | A | | 9/1999 | Bell et al. |
| 5,955,438 | A | | 9/1999 | Pitaru et al. |
| 5,964,805 | A | | 10/1999 | Stone |
| 5,968,556 | A | | 10/1999 | Atala et al. |
| 5,972,368 | A | | 10/1999 | McKay |
| 5,972,385 | A | | 10/1999 | Liu et al. |
| 5,974,663 | A | | 11/1999 | Ikeda et al. |
| 5,989,269 | A | | 11/1999 | Vibe-Hansen et al. |
| 5,989,289 | A | | 11/1999 | Coates et al. |
| 5,989,866 | A | | 11/1999 | Deisher et al. |
| 5,998,170 | A | | 12/1999 | Arakawa et al. |

6,001,352 A 12/1999 Boyan et al.
6,005,161 A 12/1999 Brekke et al.
6,013,853 A 1/2000 Athanasiou et al.
6,017,348 A 1/2000 Hart et al.
6,025,334 A 2/2000 Dupont et al.
6,025,538 A 2/2000 Yaccarino, III
6,027,743 A 2/2000 Khouri et al.
6,030,635 A 2/2000 Gertzman et al.
6,037,171 A 3/2000 Larsson
6,039,762 A 3/2000 McKay
6,060,640 A 5/2000 Pauley et al.
6,074,663 A 6/2000 Delmotte et al.
6,080,194 A 6/2000 Pachence et al.
6,090,996 A 7/2000 Li
6,090,998 A 7/2000 Grooms et al.
6,096,081 A 8/2000 Grivas et al.
6,096,347 A 8/2000 Geddes et al.
6,110,209 A 8/2000 Stone
6,110,482 A 8/2000 Khouri et al.
6,123,731 A 9/2000 Boyce et al.
6,132,472 A 10/2000 Bonutti
6,143,293 A 11/2000 Weiss et al.
6,156,068 A 12/2000 Walter et al.
6,165,486 A 12/2000 Marra et al.
6,165,487 A 12/2000 Ashkar et al.
6,180,605 B1 1/2001 Chen et al.
6,183,737 B1 2/2001 Zaleske et al.
6,189,537 B1 2/2001 Wolfinbarger, Jr.
6,197,586 B1 3/2001 Bhatnagar et al.
6,200,347 B1 3/2001 Anderson et al.
6,221,854 B1 4/2001 Radomsky
6,231,607 B1 5/2001 Ben-Bassat et al.
6,235,316 B1 5/2001 Adkisson
6,242,247 B1 6/2001 Rieser et al.
6,251,143 B1 6/2001 Schwartz et al.
6,258,778 B1 7/2001 Rodgers et al.
6,261,586 B1 7/2001 McKay
6,267,786 B1 7/2001 Stone
6,270,528 B1 8/2001 McKay
6,274,090 B1 8/2001 Coelho et al.
6,274,663 B1 8/2001 Hosokawa et al.
6,274,712 B1 8/2001 Springer et al.
6,280,473 B1 8/2001 Lemperle et al.
6,281,195 B1 8/2001 Rueger et al.
6,283,980 B1 9/2001 Vibe-Hansen et al.
6,293,970 B1 9/2001 Wolfinbarger, Jr.
6,294,187 B1 9/2001 Boyce et al.
6,294,359 B1 9/2001 Fiddes et al.
6,303,585 B1 10/2001 Spiro et al.
6,305,379 B1 10/2001 Wolfinbarger, Jr.
6,306,174 B1 10/2001 Gie et al.
6,306,424 B1 10/2001 Vyakarnam et al.
6,310,267 B1 10/2001 Rapp
6,319,712 B1 11/2001 Meenen et al.
6,333,029 B1 12/2001 Vyakarnam et al.
6,352,558 B1 3/2002 Spector
6,352,971 B1 3/2002 Deisher et al.
6,361,565 B1 3/2002 Bonutti
6,376,244 B1 4/2002 Atala
6,379,367 B1 4/2002 Vibe-Hansen et al.
6,379,385 B1 4/2002 Kalas et al.
6,383,221 B1 5/2002 Scarborough
6,387,693 B2 5/2002 Rieser et al.
6,398,811 B1 6/2002 McKay
6,398,816 B1 6/2002 Breitbart et al.
6,398,972 B1 6/2002 Blasetti et al.
6,432,436 B1 8/2002 Gertzman et al.
6,437,018 B1 8/2002 Gertzman et al.
6,440,141 B1 8/2002 Philippon
6,440,427 B1 8/2002 Wadstrom
6,440,444 B2 8/2002 Boyce et al.
6,454,811 B1 9/2002 Sherwood et al.
6,458,144 B1 10/2002 Morris et al.
6,458,158 B1 10/2002 Anderson et al.
6,458,375 B1 10/2002 Gertzman et al.
6,468,314 B2 10/2002 Schwartz
6,471,993 B1 10/2002 Shastri et al.
6,475,175 B1 11/2002 Rivera et al.
6,486,377 B2 11/2002 Rapp
6,488,033 B1 12/2002 Cerundolo
6,489,165 B2 12/2002 Bhatnagar
6,497,726 B1 12/2002 Carter et al.
6,503,277 B2 1/2003 Bonutti
6,511,511 B1 1/2003 Slivka et al.
6,511,958 B1 1/2003 Atkinson et al.
6,514,514 B1 2/2003 Atkinson et al.
6,520,964 B2 2/2003 Tallarida et al.
6,530,956 B1 3/2003 Mansmann
6,534,084 B1 3/2003 Vyakarnam et al.
6,541,024 B1 4/2003 Kadiyala et al.
6,548,729 B1 4/2003 Seelich et al.
6,569,172 B2 5/2003 Asculai et al.
6,576,015 B2 6/2003 Geistlich et al.
6,582,960 B1 6/2003 Martin et al.
6,591,581 B2 7/2003 Schmieding
6,592,598 B2 7/2003 Vibe-Hansen et al.
6,592,599 B2 7/2003 Vibe-Hansen et al.
6,599,300 B2 7/2003 Vibe-Hansen et al.
6,599,301 B2 7/2003 Vibe-Hansen et al.
6,599,515 B1 7/2003 Delmotte
6,623,963 B1 9/2003 Muller et al.
6,626,950 B2 9/2003 Brown et al.
6,630,000 B1 10/2003 Bonutti
6,632,247 B2 10/2003 Boyer, II et al.
6,652,592 B1 11/2003 Grooms et al.
6,652,593 B2 11/2003 Boyer, II et al.
6,652,872 B2 11/2003 Nevo et al.
6,662,805 B2 12/2003 Frondoza et al.
6,666,892 B2 12/2003 Hiles et al.
6,686,184 B1 2/2004 Anderson et al.
6,689,747 B2 2/2004 Filvaroff et al.
6,696,073 B2 2/2004 Boyce et al.
6,712,851 B1 3/2004 Lemperle et al.
6,727,224 B1 4/2004 Zhang et al.
6,730,314 B2 5/2004 Jeschke et al.
6,734,018 B2 5/2004 Wolfinbarger, Jr. et al.
6,743,232 B2 6/2004 Overaker et al.
6,752,834 B2 6/2004 Geistlich et al.
6,761,739 B2 7/2004 Shepard
6,761,887 B1 7/2004 Kavalkovich et al.
6,767,369 B2 7/2004 Boyer, II et al.
6,776,800 B2 8/2004 Boyer, II et al.
6,783,712 B2 8/2004 Slivka et al.
6,808,585 B2 10/2004 Boyce et al.
6,815,416 B2 11/2004 Carney et al.
6,838,440 B2 1/2005 Stiles
6,841,150 B2 1/2005 Halvorsen et al.
6,852,114 B2 2/2005 Cerundolo
6,852,125 B2 2/2005 Simon et al.
6,852,331 B2 2/2005 Lai et al.
6,855,167 B2 2/2005 Shimp et al.
6,855,169 B2 2/2005 Boyer, II et al.
6,858,042 B2 2/2005 Nadler et al.
6,866,668 B2 3/2005 Giannetti et al.
6,884,428 B2 4/2005 Binette et al.
6,890,354 B2 5/2005 Steiner et al.
6,893,462 B2 5/2005 Buskirk et al.
6,902,578 B1 6/2005 Anderson et al.
6,911,212 B2 6/2005 Gertzman et al.
6,932,977 B2 8/2005 Heidaran et al.
6,933,326 B1 8/2005 Griffey et al.
6,933,328 B2 8/2005 Schacht 6,949,252 B2 9/2005 Mizuno et al.
6,989,034 B2 1/2006 Hammer et al.
6,995,013 B2 2/2006 Connelly et al.
7,009,039 B2 3/2006 Yayon et al.
7,018,416 B2 3/2006 Hanson et al.
7,033,587 B2 4/2006 Halvorsen et al.
7,041,641 B2 5/2006 Rueger et al.
7,044,968 B1 5/2006 Yaccarino, III et al.
7,045,141 B2 5/2006 Merboth et al.
7,048,750 B2 5/2006 Vibe-Hansen et al.
7,048,762 B1 5/2006 Sander et al.
7,048,765 B1 5/2006 Grooms et al.
7,067,123 B2 6/2006 Gomes et al.
7,070,942 B2 7/2006 Heidaran et al.
7,078,232 B2 7/2006 Konkle et al.
7,108,721 B2 9/2006 Huckle et al.
RE39,321 E 10/2006 MacPhee et al.
7,115,146 B2 10/2006 Boyer, II et al.
7,125,423 B2 10/2006 Hazebrouck
7,132,110 B2 11/2006 Kay et al.
7,137,989 B2 11/2006 Asculai et al.
7,141,072 B2 11/2006 Coeistlich
7,156,880 B2 1/2007 Evans et al.
7,157,428 B2 1/2007 Kusanagi et al.
7,163,563 B2 1/2007 Schwartz et al.
7,166,133 B2 1/2007 Evans et al.
7,179,299 B2 2/2007 Edwards et al.
7,182,781 B1 2/2007 Bianchi et al.
7,201,917 B2 4/2007 Malaviya et al.
7,217,294 B2 5/2007 Kusanagi et al.
7,220,558 B2 5/2007 Luyten et al.
7,241,316 B2 7/2007 Evans et al.
7,252,987 B2 8/2007 Bachalo et al.
7,264,634 B2 9/2007 Schmieding
7,288,406 B2 10/2007 Bogin et al.
7,291,169 B2 11/2007 Hodorek
7,297,161 B2 11/2007 Fell
7,316,822 B2 1/2008 Binette et al.
7,323,011 B2 1/2008 Shepard et al.
7,323,445 B2 1/2008 Zhang et al.
7,335,508 B2 2/2008 Yayon et al.
7,338,492 B2 3/2008 Singhatat
7,338,524 B2 3/2008 Fell et al.
7,358,284 B2 4/2008 Griffey et al.
7,361,195 B2 4/2008 Schwartz et al.
7,365,051 B2 4/2008 Paulista et al.
7,371,400 B2 5/2008 Borenstein et al.
7,416,889 B2 8/2008 Ciombor et al.
7,468,075 B2 12/2008 Lang et al.
7,468,192 B2 12/2008 Mizuno et al.
7,479,160 B2 1/2009 Branch et al.
7,485,310 B2 2/2009 Luyten et al.
7,488,348 B2 2/2009 Truncale et al.
7,513,910 B2 4/2009 Buskirk et al.
7,531,000 B2 5/2009 Hodorek
7,537,617 B2 5/2009 Bindsell et al.
7,537,780 B2 5/2009 Mizuno et al.
7,550,007 B2 6/2009 Malinin
7,563,455 B2 7/2009 McKay
7,563,769 B2 7/2009 Bogin et al.
7,601,173 B2 10/2009 Messerli et al.
7,608,113 B2 10/2009 Boyer, II et al.
7,621,963 B2 11/2009 Simon et al.
7,622,438 B1 11/2009 Lazarov et al.
7,622,562 B2 11/2009 Thorne et al.
7,628,851 B2 12/2009 Armitage et al.
7,632,311 B2 12/2009 Seedhom et al.
7,638,486 B2 12/2009 Lazarov et al.
7,642,092 B2 1/2010 Maor
7,648,700 B2 1/2010 Vignery et al.
7,648,965 B2 1/2010 Vignery et al.
7,658,768 B2 2/2010 Miller et al.
7,662,184 B2 2/2010 Edwards et al.
7,666,230 B2 2/2010 Orban et al.
2001/0005592 A1 6/2001 Bhatnagar et al.
2001/0006634 A1 7/2001 Zaleske et al.
2001/0010023 A1 7/2001 Schwartz et al.
2001/0011131 A1 8/2001 Luyten et al.
2001/0016646 A1 8/2001 Rueger et al.
2001/0018619 A1 8/2001 Enzerink et al.
2001/0020188 A1 9/2001 Sander
2001/0021875 A1 9/2001 Enzerink et al.
2001/0031254 A1 10/2001 Bianchi et al.
2001/0039457 A1 11/2001 Boyer, II et al.
2001/0039458 A1 11/2001 Boyer, II et al.
2001/0043940 A1 11/2001 Boyce et al.
2001/0051834 A1 12/2001 Frondoza et al.
2002/0009805 A1 1/2002 Nevo et al.
2002/0016592 A1 2/2002 Branch et al.
2002/0035401 A1 3/2002 Boyce et al.
2002/0042373 A1 4/2002 Carney et al.
2002/0045940 A1 4/2002 Giannetti et al.
2002/0055783 A1 5/2002 Tallarida et al.
2002/0072806 A1 6/2002 Buskirk et al.
2002/0082704 A1 6/2002 Cerundolo
2002/0099448 A1 7/2002 Hiles et al.
2002/0106393 A1 8/2002 Bianchi et al.
2002/0111695 A1 8/2002 Kandel
2002/0120274 A1 8/2002 Overaker et al.
2002/0138143 A1 9/2002 Grooms et al.
2002/0177224 A1 11/2002 Madry et al.
2002/0192263 A1 12/2002 Merboth et al.
2003/0021827 A1 1/2003 Malaviya et al.
2003/0023316 A1 1/2003 Brown et al.
2003/0032961 A1 2/2003 Pelo et al.
2003/0033021 A1 2/2003 Plouhar et al.
2003/0033022 A1 2/2003 Plouhar et al.
2003/0036797 A1 2/2003 Malaviya et al.
2003/0036801 A1 2/2003 Schwartz et al.
2003/0039695 A1 2/2003 Geistlich et al.
2003/0040113 A1 2/2003 Mizuno et al.
2003/0044444 A1 3/2003 Malaviya et al.
2003/0049299 A1 3/2003 Malaviya et al.
2003/0050709 A1 3/2003 Noth et al.
2003/0055502 A1 3/2003 Lang et al.
2003/0078617 A1 4/2003 Schwartz et al.
2003/0099620 A1 5/2003 Zaleske et al.
2003/0144743 A1 7/2003 Edwards et al.
2003/0229400 A1 12/2003 Masuda et al.
2003/0236573 A1 12/2003 Evans et al.
2004/0028717 A1 2/2004 Sittinger et al.
2004/0033212 A1 2/2004 Thomson et al.
2004/0039447 A1 2/2004 Simon et al.
2004/0044408 A1 3/2004 Hungerford et al.
2004/0062753 A1 4/2004 Rezania et al.
2004/0078090 A1 4/2004 Binette et al.
2004/0102850 A1 5/2004 Shepard
2004/0115172 A1 6/2004 Bianchi et al.
2004/0134502 A1 7/2004 Mizuno et al.
2004/0138748 A1 7/2004 Boyer, II et al.
2004/0143344 A1 7/2004 Malaviya et al.
2004/0151705 A1 8/2004 Mizuno et al.
2004/0166169 A1 8/2004 Malaviya et al.
2004/0170610 A1 9/2004 Slavin et al.
2004/0175826 A1 9/2004 Maor
2004/0192605 A1 9/2004 Renwen et al.
2004/0193268 A1 9/2004 Hazebrouck
2004/0197311 A1 10/2004 Brekke et al.
2004/0197373 A1 10/2004 Gertzman et al.
2004/0219182 A1 11/2004 Gomes et al.
2004/0220574 A1 11/2004 Pelo et al.
2004/0230303 A1 11/2004 Gomes et al.

2004/0243242 A1 12/2004 Sybert et al.
2005/0004672 A1 1/2005 Pafford et al.
2005/0020500 A1 1/2005 Shen et al.
2005/0027307 A1 2/2005 Schwartz et al.
2005/0043814 A1 2/2005 Kusanagi et al.
2005/0064042 A1 3/2005 Vunjak-Novakovia et al.
2005/0074476 A1 4/2005 Gendler et al.
2005/0074481 A1 4/2005 Brekke et al.
2005/0089544 A1 4/2005 Khouri et al.
2005/0101957 A1 5/2005 Buskirk et al.
2005/0112761 A1 5/2005 Halvorsen et al.
2005/0129668 A1 6/2005 Giannetti et al.
2005/0152882 A1 7/2005 Kizer et al.
2005/0159820 A1 7/2005 Yoshikawa et al.
2005/0159822 A1 7/2005 Griffey et al.
2005/0196460 A1 9/2005 Malinin
2005/0209705 A1 9/2005 Niederauer et al.
2005/0222687 A1 10/2005 Vunjak-Novakovia et al.
2005/0228498 A1 10/2005 Andres
2005/0240281 A1 10/2005 Slivka et al.
2005/0251268 A1 11/2005 Truncale
2005/0260612 A1 11/2005 Padmini et al.
2005/0261681 A9 11/2005 Branch et al.
2005/0261767 A1 11/2005 Anderson et al.
2005/0288796 A1 12/2005 Awad et al.
2006/0030948 A1 2/2006 Manrique et al.
2006/0060209 A1 3/2006 Shepard
2006/0099234 A1 5/2006 Winkler
2006/0111778 A1 5/2006 Michalow
2006/0167483 A1 7/2006 Asculai et al.
2006/0178748 A1 8/2006 Dinger, III et al.
2006/0200166 A1 9/2006 Hanson et al.
2006/0210643 A1 9/2006 Truncale et al.
2006/0216323 A1 9/2006 Knaack et al.
2006/0216822 A1 9/2006 Mizuno et al.
2006/0235534 A1 10/2006 Gertzman et al.
2006/0247790 A1 11/2006 McKay
2006/0247791 A1 11/2006 McKay et al.
2006/0251631 A1 11/2006 Adkisson, IV et al.
2006/0276907 A1 12/2006 Boyer, II et al.
2007/0009610 A1 1/2007 Syring
2007/0014867 A1 1/2007 Kusanagi et al.
2007/0026030 A1 2/2007 Gill et al.
2007/0036834 A1 2/2007 Pauletti et al.
2007/0041950 A1 2/2007 Leatherbury et al.
2007/0055377 A1 3/2007 Hanson et al.
2007/0065943 A1 3/2007 Smith et al.
2007/0067032 A1 3/2007 Felt et al.
2007/0083266 A1 4/2007 Lang
2007/0093896 A1 4/2007 Malinin
2007/0093912 A1 4/2007 Borden
2007/0098759 A1 5/2007 Malinin
2007/0100045 A1 5/2007 Hodorek
2007/0113951 A1 5/2007 Huang
2007/0128155 A1 6/2007 Seyedin
2007/0134291 A1 6/2007 Ting
2007/0135917 A1 6/2007 Malinin
2007/0135918 A1 6/2007 Malinin
2007/0135928 A1 6/2007 Malinin
2007/0148242 A1 6/2007 Vilei et al.
2007/0162121 A1 7/2007 Tarrant et al.
2007/0168030 A1 7/2007 Edwards et al.
2007/0172506 A1 7/2007 Nycz et al.
2007/0179601 A1 8/2007 Hodorek et al.
2007/0185585 A1 8/2007 Bracy et al.
2007/0276506 A1 11/2007 Troxel
2007/0299517 A1 12/2007 Davisson et al.
2007/0299519 A1 12/2007 Schmieding
2008/0015709 A1 1/2008 Evans et al.
2008/0027546 A1 1/2008 Semler et al.
2008/0031915 A1 2/2008 Becerra Ratia et al.
2008/0038314 A1 2/2008 Hunziker
2008/0039939 A1 2/2008 Iwamoto et al.
2008/0039954 A1 2/2008 Long et al.
2008/0039955 A1 2/2008 Hunziker
2008/0051889 A1 2/2008 Hodorek
2008/0065210 A1 3/2008 McKay
2008/0077251 A1 3/2008 Chen et al.
2008/0119947 A1 5/2008 Huckle et al.
2008/0125863 A1 5/2008 McKay
2008/0125868 A1 5/2008 Branemark
2008/0138414 A1 6/2008 Hunckle et al.
2008/0153157 A1 6/2008 Yao et al.
2008/0154372 A1 6/2008 Peckham
2008/0167716 A1 7/2008 Schwartz et al.
2008/0183300 A1 7/2008 Seedhom et al.
2008/0305145 A1 12/2008 Shelby et al.
2009/0043389 A1 2/2009 Vunjak-Novakovic et al.
2009/0069901 A1 3/2009 Truncale et al.
2009/0069904 A1 3/2009 Picha
2009/0076624 A1 3/2009 Rahaman et al.
2009/0081276 A1 3/2009 Alsberg et al.
2009/0099661 A1 4/2009 Bhattacharya et al.
2009/0117652 A1 5/2009 Luyten et al.
2009/0131986 A1 5/2009 Lee et al.
2009/0149893 A1 6/2009 Semler et al.
2009/0210057 A1 8/2009 Liao et al.
2009/0226523 A1 9/2009 Behnam et al.
2009/0280179 A1 11/2009 Neumann et al.
2009/0299475 A1 12/2009 Yamamoto et al.
2009/0312805 A1 12/2009 Lang et al.
2009/0312842 A1 12/2009 Bursac et al.
2009/0319051 A9 12/2009 Nycz et al.
2010/0021521 A1 1/2010 Xu et al.
2010/0036492 A1 2/2010 Hung et al.
2010/0036503 A1 2/2010 Chen et al.

FOREIGN PATENT DOCUMENTS

EP 0762903 A1 12/1995
EP 0517030 B1 9/1996
EP 0739631 A2 10/1996
EP 0784985 A1 7/1997
EP 0968012 A1 9/1998
EP 1719531 A2 5/2001
EP 1237511 B1 6/2001
EP 1237511 A1 6/2001
EP 1127581 A1 8/2001
EP 1181908 A1 2/2002
EP 1234552 A1 8/2002
EP 1234555 A2 8/2002
EP 0739631 B1 3/2003
EP 1181908 B1 12/2003
EP 1384452 A1 1/2004
EP 1234555 A3 6/2004
EP 1618178 A1 11/2004
EP 1127581 B1 6/2005
EP 1561481 A2 8/2005
EP 1618178 B1 1/2006
EP 1234552 B1 8/2006
EP 0968012 B1 9/2006
EP 1719463 A1 11/2006
EP 1719532 A2 11/2006
EP 1234555 B1 2/2007
EP 0762903 B2 8/2007
EP 1537883 B1 4/2008
GB 2102811 A1 2/1983
SU 1454423 A1 1/1989
WO WO 84/04880 A1 12/1984
WO 90/01342 A1 2/1990
WO 93/16739 A1 9/1993
WO WO 94/03584 A1 2/1994
WO 95/25748 A1 9/1995

| | | | |
|---|---|---|---|
| WO | WO 95/33502 | A1 | 12/1995 |
| WO | 95/24310 | A1 | 8/1996 |
| WO | WO 98/14222 | A1 | 4/1998 |
| WO | WO 98/41246 | A2 | 9/1998 |
| WO | 98/43686 | A1 | 10/1998 |
| WO | WO 99/09914 | A1 | 3/1999 |
| WO | WO 99/11298 | A2 | 3/1999 |
| WO | 99/15209 | A1 | 4/1999 |
| WO | WO 99/21497 | A1 | 5/1999 |
| WO | WO 99/22747 | | 5/1999 |
| WO | WO 99/48541 | A1 | 9/1999 |
| WO | WO 99/52572 | A1 | 10/1999 |
| WO | 99/56797 | A1 | 11/1999 |
| WO | WO 00/40177 | A1 | 7/2000 |
| WO | 00/47114 | A1 | 8/2000 |
| WO | 01/07595 | A2 | 2/2001 |
| WO | 01/38357 | A2 | 5/2001 |
| WO | 01/39788 | A2 | 6/2001 |
| WO | 01/46416 | A1 | 6/2001 |
| WO | WO 01/043667 | A1 | 6/2001 |
| WO | 02/18546 | A2 | 3/2002 |
| WO | 02/22779 | A2 | 3/2002 |
| WO | 02/95019 | A1 | 3/2002 |
| WO | 02/36732 | A2 | 5/2002 |
| WO | WO 02/058484 | A2 | 8/2002 |
| WO | WO 02/064180 | A1 | 8/2002 |
| WO | 02/077199 | A2 | 10/2002 |
| WO | 02/095019 | A1 | 11/2002 |
| WO | WO 03/007805 | A2 | 1/2003 |
| WO | WO 03/007805 | A3 | 1/2003 |
| WO | 03/007873 | A2 | 1/2003 |
| WO | WO 03/007879 | A2 | 1/2003 |
| WO | WO 03/007879 | A3 | 1/2003 |
| WO | 03/012053 | A2 | 2/2003 |
| WO | 03/079985 | A2 | 10/2003 |
| WO | 03/087160 | A1 | 10/2003 |
| WO | 03/094835 | A2 | 11/2003 |
| WO | 2004/067704 | A2 | 8/2004 |
| WO | 2004/069298 | A1 | 8/2004 |
| WO | WO 2004/075940 | A1 | 9/2004 |
| WO | WO 2004/096983 | A2 | 11/2004 |
| WO | WO 2004/096983 | A3 | 11/2004 |
| WO | WO 2004/103224 | A1 | 12/2004 |
| WO | 2005058207 | A1 | 6/2005 |
| WO | WO 2005/110278 | A3 | 11/2005 |
| WO | WO 2005/110278 | A2 | 11/2005 |
| WO | WO 2006/042311 | A3 | 4/2006 |
| WO | WO 2006/042311 | A2 | 4/2006 |
| WO | 2006/050213 | A2 | 5/2006 |
| WO | 02/36732 | A3 | 9/2006 |
| WO | 2006/113586 | A2 | 10/2006 |
| WO | 03/094835 | A3 | 12/2006 |
| WO | WO 2007/024238 | A1 | 3/2007 |
| WO | 2006/113586 | A3 | 9/2007 |
| WO | 2008/013763 | A2 | 1/2008 |
| WO | WO 2008/021127 | A2 | 2/2008 |
| WO | 2008/038287 | A2 | 4/2008 |
| WO | 2008/013763 | A3 | 6/2008 |
| WO | 2008/081463 | A2 | 7/2008 |
| WO | 2008/038287 | A3 | 9/2008 |
| WO | WO 2008/106254 | A2 | 9/2008 |
| WO | WO 2009/076164 | A2 | 6/2009 |
| WO | WO 2009/111069 | A3 | 9/2009 |

OTHER PUBLICATIONS

Hunziker, "Articular Cartilage Repair: Basic Science and Clinical Progress. A Review of the Current Status and Prospects", Osteoarthritis and Cartilage 2001, vol. 10, No. 6, pp. 432–463.

Chen et al., "Repair of Articular Cartilage Defects: Part I. Basic Science of Cartilage Healing", The American Journal of Orthopedics, Jan. 1999, pp. 31–33.

Chen et al., "Repair of Articular Cartilage Defects: Part II. Treatment Options", The American Journal of Orthopedics, Feb. 1999, pp. 88–96.

Buckwalter, "Articular Cartilage Injuries", Clinical Orthopaedics and Related Research, 2002, No. 402, pp. 21–37.

Nixon et al., "New Horizons in Articular Cartilage Repair", Proceedings of the Annual Convention of the AAEP, 2001, vol. 47, pp. 217–226.

Tsumaki et al., "Role of CDMP–1 in Skeletal Morphogenesis: Promotion of Mesenchymal Cell Recruitment and Chondrocyte Differentiation", J. Cell Biol., Jan. 1999, vol. 144, No. 1, 161–173.

Feczko et al., "Experimental Results of Donor Site Filling for Autologous Osteochondral Mosaicplasty", Arthroscopy: The Journal of Arthroscopic and Related Surgery, vol. 19, No. 7 (Sep. 2003), pp. 755–761.

Peretti et al., "Cell–Based Bonding of Articular Cartilage: An Extended Study", Journal of Biomedical Materials Research, 64A, 2003, pp. 517–524.

Peretti et al., "Cell–Based Tissue–Engineered Allogeneic Implant for Cartilage Repair", Tissue Engineering, 2000, vol. 6, No. 5, pp. 567–576.

Bugbee, "Fresh Osteochondral Allografting", Operative Techniques in Sports Medicine, Apr. 2000, vol. 8, No. 2, pp. 158–162.

Jackson et al., "Cartilage Substitutes: Overview of Basic Science & Treatment Options", Journal of American Academy of Orthopaedic Surgeons, vol. 9, Jan./Feb. 2001, pp. 37–52.

Verbruggen et al., "Repair Function in Organ Cultured Human Cartilage. Replacement of Enzymatically Removed Proteoglycans During Longterm Organ Culture", The Journal of Rheumatology, 12:4, 1985, pp. 665–674.

Glowacki, "Engineered Cartilage, Bone, Joints and Menisci—Potential for Temporomandibular Joint Reconstruction", Cells Tissues Organs, vol. 169, Issue 3, 2001, pp. 302–308.

Peretti et al., "A Biomechanical Analysis of an Engineered Cell–Scaffold Implant for Cartilage Repair", Annals of Plastic Surgery, 2001, vol. 46, No. 5, pp. 533–537.

Peretti et al., "A Biomechanical Analysis of a Chondrocyte–Based Repair Model of Articular Cartilage", Tissue Engineering, Aug. 1, 1999, vol. 5, No. 4, pp. 317–326.

Peretti et al., "In Vitro Bonding of Pre–seeded Chondrocytes", Sport Sciences for Health, May 1, 2007, vol. 2, No. 1, pp. 29–33.

Peretti et al., "Bonding of Cartilage Matrices with Cultured Chondrocytes: An Experimental Model", Journal of Orthopedic Research, Jan. 1998, vol. 16, No. 1, pp. 89–95.

Nettles et al., "In Situ Crosslinkable Hyaluronan For Articular Cartilage Repair", 50th Annual Meeting of the Orthopaedic Research Society, (Mar. 2004) Paper No. 0202.

Nettles et al., "Photocrosslinkable Hyaluronan As a Scaffold for Articular Cartilage Repair", Annals of Biomedical Engineering, vol. 32, No. 3, Mar. 2004, pp. 391–397.

Girotto et al., "Tissue–specific gene expression in chondrocytes grown on three–dimensional hyaluronic acid scaffolds", Biomaterials, vol. 24 (2003), pp. 3265–3275.

Gertzman et al., "A pilot study evaluating sodium hyaluronate as a carrier for freeze–dried demineralized bone powder", Cell and Tissue Banking, vol. 2, 2001, pp. 87–94.

Trzeciak et al., "Evaluation of Cartilage Reconstruction by Means of Autologous Chondrocyte Versus Periosteal Graft Transplantation: An Animal Study", Transplantation Proceedings, vol. 38 (2006), pp. 305–311.
Brighton et al., "Articular Cartilage Preservation and Storage—I. Application of Tissue Culture Techniques to the Storage of Viable Articular Cartilage", Arthritis and Rheumatism, vol. 22, No. 10 (Oct. 1979) pp. 1093–1101.
Mahadev et al., "Autogenous Osteochondral Morselised Grafts for Full Thickness Osteochondral Defects in the Knee Joints of Pigs", Singapore Medical Journal, 2001, vol. 42(9), pp. 410–416.
Hunziker, "Articular Cartilage Structure in Humans and Experimental Animals", *Articular Cartilage and Osteoarthritis,* Raven Press, ed., 1992, pp. 183–199.
Diduch et al., "Joint Repair: Treatment Options for Articular Cartilage Injury" Orthopedic Technology Review (2002) 4:24–27.
Stone, et al., "One–step American Technique of Articular Cartilage Paste Grafting to Traumatic and Arthritic Defects in the Knee Joint (2–7 Years Follow Up)", downloaded from http://www.stoneclinic.com/onestep.htm, publication date unavailable. Downloaded Apr. 4, 2008.
Gilbert, et al., "Decellularization of Tissue and Organs", Biomaterials (2006) 27:3675–3683.
Non–final Office Action mailed on Feb. 6, 2007 in connection with U.S. Appl. No. 10/438,883.
Non–final Office Action mailed on Nov. 5, 2004 in connection with U.S. Appl. No. 10/438,883.
Office Action issued on Apr. 24, 2007 in connection with Australian Patent Application No. 2004235291.
Non–final Office Action mailed on May 3, 2005 in connection with U.S. Appl. No. 10/438,883.
Final Office Action mailed on Oct. 18, 2005 in connection with U.S. Appl. No. 10/438,883.
USPTO Communication mailed Oct. 9, 2007 in connection with U.S. Appl. No. 10/438,883.
Non–final Office Action mailed on Apr. 19, 2007 in connection with U.S. Appl. No. 11/151,270.
Final Office Action mailed on Oct. 9, 2007 in connection with U.S. Appl. No. 11/151,270.
Advisory Action mailed on Dec. 27, 2007 in connection with U.S. Appl. No. 11/151,270.
Office Action mailed Feb. 7, 2008 in connection with U.S. Appl. No. 10/815,778.
Non–final Office Action mailed on Feb. 20, 2007 in connection with U.S. Appl. No. 10/960,960.
Final Office Action mailed on Sep. 28, 2007 in connection with U.S. Appl. No. 10/960,960.
Non–final Office Action mailed on Dec. 18, 2007 in connection with U.S. Appl. No. 11/081,103.
Office Action issued on Nov. 7, 2007 in connection with New Zealand Patent Application No. 543665.
U.S. Appl. No. 12/010,984, filed Jan. 31, 2008 titled Cartilage Repair Mixture Containing Allograft Chondroctypes.
U.S. Appl. No. 11/657,042, filed Jan. 24, 2007 titled Two Piece Cancellous Construct for Cartilage Repair.
U.S. Appl. No. 12/043,001, filed Mar. 5, 2008 Cancellous Construct with Support Ring for Repair of Osteochondral Defects.
U.S. Appl. No. 12/079,629, filed Mar. 26, 2008 Titled Cartilage Implant Plug with Fibrin Glue and Method for Implantation.
International Search Report issued in connection with International Patent Application No. PCT/US2004/010957 Application on Nov. 1, 2004.
International Preliminary Report on Patentability issued on Nov. 18, 2005 in connection with International Patent Application No. PCT/US2004/010957.
International Search Report issued in connection with International Patent Application No. PCT/US2005/030610 on Apr. 7, 2006.
Written Opinion issued on Apr. 7, 2006 in connection with International Patent Application No. PCT/US2005/030610.
International Search Report issued on Sep. 21, 2006 in connection with International Patent Application No. PCT/US2005/036878.
International Preliminary Report on Patentability issued on Apr. 17, 2007 2006 in connection with International Patent Application No. PCT/US2005/036878.
Office Action issued on Sep. 8, 2006 in connection with European Patent Application No. 04749924.9.
Supplementary European Search Report issued on Jun. 28, 2006 in connection with European Patent Application No. 04749924.9.
International Search Report issued in connection with International Patent Application No. PCT/US2005/008798 on Jun. 19, 2006.
Written Opinion issued in connection with International Patent Application No. PCT/US2005/008798 on Jun. 19, 2006.
International Preliminary Report on Patentability issued in connection with International Patent Application No. PCT/US2005/008798 on Nov. 1, 2006.
International Search Report issued in connection with International Patent Application No. PCT/US2004/010956 on Oct. 28, 2005.
Written Opinion issued in connection with International Patent Application No. PCT/US2004/010956 on Oct. 28, 2005.
International Preliminary Report on Patentability issued on Nov. 18, 2005 in connection with International Patent Application No. PCT/US2004/010956.
International Patent Application No. PCT/US2008/051796 filed Jan. 23, 2008 titled Two Piece Cancellous Construct for Cartilage Repair.
Written Opinion issued in connection with International Patent Application No. PCT/US2004/010957 on Nov. 1, 2004.
International Preliminary Report on Patentability issued on Feb. 26, 2008 in connection with International Patent Application No. PCT/US2005/030610.
Written Opinion issued in connection with International Patent Application No. PCT/US2005/036878 on Sep. 21, 2006.
Hoffman, "Hydrogels for Biomedical Applications", Advanced Drug Delivery Reviews, 2002, vol. 43, pp. 3–12.
Dahlberg et al., "Demineralized Allogeneic Bone Matrix for Cartilage Repair", Journal of Orthopaedic Research, 1991, vol. 9, pp. 11–19.
Lu et al., "Minced Cartilage without Cell Culture Serves as an Effective Intraoperative Cell Source for Cartilage Repair", Journal of Orthopaedic Research, Jun. 2006, vol. 24, pp. 1261–1270.

Stone et al., "Articular Cartilage Paste Grafting to Full–Thickness Articular Cartilage Knee Joint Lesions: A 2– to 12–Year Follow–up", Arthroscopy: The Journal of Arthoscopic and Related Surgery, Mar. 2006, vol. 22, No. 3, pp. 291–299.

Newman, "Articular Cartilage Repair", American Journal of Sports Medicine, 1998, vol. 26, No. 2, pp. 309–324.

Brittberg et al., "Treatment of Deep Cartilage Defects in the Knee with Autologous Chondrocyte Transplantation", New England Journal of Medicine, Oct. 6, 1994, vol. 331, No. 14, pp. 889–895.

Nixon et al., "Enhanced Repair of Extensive Articular Defects by Insulin–like Growth Factor–I–Laden Fibrin Composites", Journal of Orthopaedic Research, 1999; 17:475–487.

International Cartilage Repair Society, "Cartilage Injury Evaluation Package", www.cartilage.org, 2000.

Richardson et al., "Repair of Human Articular Cartilage After Implantation of Autologous Chondrocytes", Journal of Bone and Joint Surgery [Br], 1999, 81–B:1064–1068.

Brittberg et al., "Autologous Chondrocytes Used for Articular Cartilage Repair: An Update", Clinical Orthopaedics and Related Research, 2001; No. 391 Suppl: S337–S348.

Peterson et al., "Two– to 9–year Outcome After Autologous Chondrocyte Transplantation of the Knee", Clinical Orthopaedic and Related Research, 2000; No. 374: 212–234.

Peterson et al., "Autologous Chondrocyte Transplantation: Biomechanics and Long–term Durability", American Journal of Sports Medicine, 2002, vol. 30, No. 1, pp. 2–12.

Messner et al., "Cartilage Repair: A Critical Review", Acta Orthopaedic Scandinavica, 1996, vol. 67, No. 5, pp. 523–529.

Messner et al., "The Long–term Prognosis for Severe Damage to Weight–bearing Cartilage in the Knee: A 14–year Clinical and Radiographic Follow–up in 28 Young Athletes", Acta Orthopaedic Scandinavica, 1996, vol. 67, No. 2, pp. 165–168.

Buckwalter et al., "Articular Cartilage: Degeneration and Osteoarthritis, Repair, Regeneration, and Transplantation", AAOS Instructional Course Lectures, 1998; 47:487–504.

Breinan et al., "Effect of Cultured Autologous Chondrocytes on Repair of Chondral Defects in a Canine Model", Journal of Bone and Joint Surgery [Am], Oct. 1997; vol. 79–A, No. 10, 1439–1451.

Breinan et al., "Autologous Chondrocyte Implantation in a Canine Model: Change in Composition of Reparative Tissue with Time", Journal of Orthopaedic Research, 2001; 19:482–492.

Brittberg et al., "Rabbit Articular Cartilage Defects Treated with Autologous Cultured Chondrocytes", Clinical Orthopaedics and Related Research, 1996; 326:270–283.

Nehrer et al., "Chondrocyte–seeded Collagen Matrices Implanted in a Chondral Defect in a Canine Model", Biomaterials, 1998; 19:2313–2328.

Vunjak–Novakovic et al., "Bioreactor Cultivation Conditions Modulate the Composition and Mechanical Properties of Tissue–Engineered Cartilage", Journal of Orthopaedic Research, 1999; 17:130–138.

Bursac, "Collagen Network Contributions to Structure–Function Relationships in Cartilaginous Tissues in Compression" (Dissertation), Boston University College of Engineering, 2002.

Gooch et al., "IGF–I and Mechanical Environment Interact to Modulate Engineered Cartilage Development", Biochemical and Biophysical Research Communications, 2001; 286:909–915.

Pei et al., "Growth Factors for Sequential Cellular De– and Re–differentiation in Tissue Engineering", Biochemical and Biophysical Research Comunications, 2002; 294:149–154.

Obradovic et al., "Integration of Engineered Cartilage", Journal of Orthopaedic Research, 19:1089–1097, 2001.

Schaefer et al., "Tissue Engineered Composites for tha Repair of Large Osteochondral Defects", Arthritis & Rheumatism, 46(9): 2524–2534 (2002).

Pei et al., "Bioreactors Mediate the Effectiveness of Tissue Engineering Scaffolds", The FASEB Journal, 16:1691–1694, published online (Aug. 7, 2002), 10.1096/fj.02–0083fje.

Madry et al., "Gene Transfer of a Human Insulin–like Growth Factor I cDNA Enhances Tissue Engineering of Cartilage", Human Gene Therapy, 13: 1621–1630 (Sep. 1, 2002).

Pearson et al. (eds.), American Association of Tissue Banks, Standards for Tissue Banking, 2008 ($12^{th}$ ed.), pp. 53–56, 86–88.

Ornits et al., "Protein Family Review: Fibroblast Growth Factors", Genome Biology (2001) 2(3): reviews 3005.1–3005.12, http://genomebiology.com/2001/2/3/reviews/3005.1.

Loeser et al., "Basic Fibroblast Growth Factor Inhibits the Anabolic of Insulin–like Growth Factor 1 and Osteogenic Protein 1 in Adult Human Articular Chondrocytes", Arthritis & Rheumatism, vol. 52, No. 12 (Dec. 2005), pp. 3910–3917.

Kato et al., "Fibroblast Growth Factor is an Inhibitor of Chondrocyte Terminal Defferentiation", Journal of Biological Chemistry, vol. 265, No. 10 (Apr. 5, 1990) pp. 5903–5909.

Andrés et al., "A Pro–Inflammatory Signature Mediates FGF2–induced Angiogenesis", Journal of Cellular and Molecular Medicine, (2008).

Burger et al., "Fibroblast growth factor receptor–1 is expressed by endothelial progenitor cells", Blood, vol. 100, No. 10 (Nov. 15, 2002) 3527–35.

Baird, "Fibroblast growth factors: activities and significance of non–neurotrophin neurotrophic growth factors", Current Opinions in Neurobiology, (1994) 4:78–86.

Mazué et al., "Preclinical and Clinical Studies with Recombinant Human Basic Fibroblast Growth Factor", Annals New York Academy of Sciences, (1991) 329–340.

Aviles et al., "Testing clinical therapeutic angiogenesis using basic fibroblast growth factor (FGF–2)", British Journal of Pharmacology (2003) 140: 637–646.

Nolan et al., "Living Bone Grafts", BMJ, vol. 304, Jun. 13, 1992, pp. 1520 and 1521.

Osteo Sponge product information, Bacterin International Inc., May 2005.

A non–final Office Action mailed on Jun. 8, 2009 in connection with U.S. Appl. No. 11/481,955.

A non–final Office Action mailed on Jul. 9, 2008 in connection with U.S. Appl. No. 11/151,270.

A final Office Action mailed on Nov. 13, 2008 in connection with U.S. Appl. No. 10/815,778.

A non–final Office Action mailed on Jul. 2, 2009 in connection with U.S. Appl. No. 10/815,778.

A non–final Office Action mailed on May 18, 2009 in connection with U.S. Appl. No. 11/657,042.
U.S. Appl. No. 12/381,072, filed Mar. 5, 2009 entitled "Cancellous Constructs, Cartilage Particles and Combinations of Cancellous Constructs and Cartilage Particles".
A final Office Action mailed on Sep. 19, 2008 in connection with U.S. Appl. No. 11/081,103.
U.S. Appl. No. 12/508,892, filed Jul. 24, 2009 entitled "Cancellous Constructs with Support Ring for Repair of Osteochondral Defects".
An International Search Report issued on Jun. 23, 2009 in connection with International Patent Application No. PCT/US2008/051796.
A Written Opinion issued on Jun. 23, 2009 in connection with International Patent Application No. PCT/US2008/051796.
An International Preliminary Report on Patentability issued on Jul. 28, 2009 in connection with International Patent Application No. PCT/US2008/051796.
An International Search Report issued on Jul. 6, 2009 in connection with International Patent Application No. PCT/US2008/085522.
A Written Opinion issued on Jul. 6, 2009 in connection with International Patent Application No. PCT/US2008/085522.
An International Search Report issued on Jul. 6, 2009 in connection with International Patent Application No. PCT/US2009/001459.
A Written Opinion issued on Jul. 6, 2009 in connection with International Patent Application No. PCT/US2009/001459.
Canadian Office Action issued on Aug. 24, 2009 in connection with Canadian Patent Application No. 2,563,082.
http://www.stoneclinic.com/articularcartilagepastegrafting, no date.
http://www.technobusiness–solutions.com/article–lyophilization1.html, published Feb. 12, 2002.
Non–final Office Action mailed on Jul. 22, 2009 in connection with U.S. Appl. No. 12/010,984.
Non–final Office Action mailed on Jun. 3, 2009 in connection with U.S. Appl. No. 11/081,103.
Non–Final Office Action for U.S. Appl. No. 11/081,103, mailed Jan. 14, 2010.
Final Office Action for U.S. Appl. No. 11/481,955, mailed Jan. 7, 2010.
Crescenzi et al., "Hyaluronan Linear and Crosslinked Derivatives as Potential/Actual Biomaterials", in Hyaluronan (2002), vol. 1 (Chemical, Biochemical and Biological Aspects), J. F. Kennedy et al., Ed., pp. 261–268.
Michielen et al., "Novel Biomaterials Based on Cross–linked Hyaluronan: Structural Investigations", in Hyaluronan (2002), vol. 1 (Chemical, Biochemical and Biological Aspects), J. F. Kennedy et al., Ed., pp. 269–276.
U.S. Appl. No. 12/696,366, filed Jan. 29, 2010.
U.S. Appl. No. 12/657,207, filed Jan. 14, 2010.
Office Action dated Jan. 14, 2010, received in U.S. Appl. No. 11/081,103, filed on Mar. 16, 2005.
Yee, Cindy J. et al., (2000) Analysis of fibroblast growth factor receptor 3 S249C mutation in cervical carcinoma. Journal of the National Cancer Institute 92(22):1848–1849.
Zhang, Jiandong et al., (1991) Three–dimensional structure of human basic fibroblast growth factor, a structural homolog of interleukin 1 Beta. Proc Natl Acad Sci. USA 88(8):3446–3450.
Zhu, Hengyi et al., (1995) Glu–96 of basic fibroblast growth factor is essential for high affinity receptor binding. Journal Of Biological Chemistry 270(37):21869–21874.
Zhu, Hengyi et al., (1997) Analysis of high–affinity binding determinants in the receptor binding epitope of basic fibroblast growth factor. Protein Engineering 10(4):417–421.
Carr, M. E. Jr. and Alving, B. M. (1995) Effect of fibrin structure on plasmin–mediated dissolution of plasma clots. Blood Coag, Fibrinol. 6(6):567–573.
Carr, Marcus E. (1998) Fibrin formed in plasma is composed of fibers more massive than those formed from purified fibrinogen. Thromb. Haemost. 59(3):535–539.
Cook, James L. et al., (2003) Biocompatibility of three–dimensional chondrocyte grafts in large tibial defects of rabbits. Am J Vet Res. 64(1):12–20.
Gao, Jizong et al., (2002) Repair of osteochondral defect with tissue–engineered two–phase composite material of injectable calcium phosphate and hyaluronan sponge. Tissue Engin. Part A 8(5):827–837.
Gruber, Reinhard et al., (2002) Platelets stimulate proliferation of bone cells: involvement of platelet–derived growth factor, microparticles and membranes. Clin Oral Implants Res. 13(5):529–535.
Haisch, A. et al., (2000) Preparation of a pure autologous biodegradable fibrin matrix for tissue engineering. Med Biol Eng Comput. 38(6):686–689.
Itokazu, M. et al., (1997) The sustained release of antibiotic from freeze–dried fibrin–antibioticcompound and efficacies in a rat model of osteomyelitis. Infection 25(6):359–363.
Sims, C. Derek et al., (1998) Tissue engineered neocartilage using plasma derived polymer substrates and chondrocytes. Plastic & Recon. Surg. 101(6):1580–1585.
"Young's Modulus," Entry on http://en.wikipedia.org. accessed Oct. 27, 2005. 3 pages.
Bradford, Marion M. (1976) A Rapid and Sensitive Method for the Quantitation of Microgram Quantities of Protein Utilizing the Principle of Protein–Dye Binding. Analytical Biochemistry 72(1–2):248–254.
Matsuda et al. (1995) In Vivo Chondrogenesis in Collagen Sponge Sandwiched by Perichondrium. J. Biomater. Sci. Polymer Ed., vol. 7, No. 3, pp. 221–229.
Fujisato et al., (1996) Effect of basic fibroblast growth factor on cartilage regeneration in chondrocyte–seeded collagen sponge scaffold. Biomaterials, vol. 17, No. 2, pp. 155–162.
Non–Final Office Action mailed Apr. 15, 2010 in connection with U.S. Appl. No. 12/079,629.
Non–Final Office Action mailed Apr. 12, 2010 in connection with U.S. Appl. No. 12/191,490.
Non–Final Office Action mailed Apr. 15, 2010 in connection with U.S. Appl. No. 11/657,042.
International Preliminary Report on Patentability for PCT/US2009/001459, mailed on May 12, 2010.
Atala et al., Injectable alginate seeded with chondrocytes as a potential treatment for vesicoureteral reflux, J. of Urology 150(2 Pt 2):745–7 (1993).
International Preliminary Report on Patentability for PCT/US2008/085522, mailed on Jun. 17, 2010.
Nettles et al. (Mar. 2004), "In Situ Crosslinkable Hyaluronan For Articular Cartilage Repair", 50th Annual Meeting of the Orthopaedic Research Society, Paper No. 0202.
Final Office Action for U.S. Appl. No. 11/081,103, mailed Aug. 11, 2010.
Non–final Office Action for U.S. Appl. No. 12/010,984, mailed Aug. 16, 2010.

Abraham, Judith A. et al., (1986) Human Basic Fibroblast Growth Factor: Nucleotide Sequence And Genomic Organization. EMBO Journal 5(10):2523–2528.
Agrawal, Sudhir et al., (1991) Pharmacokinetics. Biodistribution, And Stability Of Oligodeoxynucleotide Phosphorothioates In Mice. Proc Natl Acad Sci. USA 88(17):7595–7599.
Arakawa, Tsutomu et al., (1993) Production and Characterization of an Analog of Acidic Fibroblast Growth Factor With Enhanced Stability and Biological Activity. Protein Engineering 6(5):541–546.
Bailly, Karine et al., (2000) Uncoupling of cell proliferation and differentiation activities of basic fibroblast growth factor. FASEB Journal 14(2):333–343.
Bange, Johannes et al., (2002) Cancer progression and tumor cell motility are associated with the FGFR4 Arg388 Allele. Cancer Research 62(3):840–846.
Bork, Peer (2000) Powers and pitfalls in sequence analysis: The 70% hurdle. Genome Res. 10(4):398–400.
Bork, Peer and Bairoch, Amnon (1996) Go hunting in sequence databases but watch out for the traps. Trends in Genetics 12(10):425–427.
Brenner, Steven E. (1999) Errors in genome annotation. Trends in Genetics 15(4):132–133.
Cappellen, David et al., (1999) Frequent activating mutations of FGFR3 In human bladder arid cervix carcinomas. Nature Genetics 23(1):18–20.
Chusho, Hideki et al., (2001) Dwarfism and earlydeath in mice lacking C–type Natriuretic Peptide. Proc Natl Acad Sci. 98(7):4016–4021.
Coughlin, Shaun R. et al., (1988) Acidic and basic fibroblast growth factors stimulate tyrosine kinase activity in vivo. J Biol Chem. 263(2):988–993.
Dell'Accio, Francesco et al., (2001) Molecular markers predictive of the capacity of expanded human articular chondrocytes to form stable cartilage in vivo, Arthritis Rheum. 44(7):1608–19.
Doerks, Tobias et al., (1998) Protein annotation: detective work for function prediction. Trends Genet. 14(6):248–250.
Dvorakova, Dana et al., (2001) Changes in the expression of FGFR3 in patients with chronic myeloid leukaemia receiving transplant of allogeneic peripheral blood stem cells__ British Journal Haematology 13(3):832–835.
Eriksson, A. Elisabeth et al., (1991) Three–dimensional structure of human basic fibroblast growth factor. Proc. Natl. Acad. Sci. USA 88:3441–3445 (XP002936511).
Ezzat Shereen et al., (2002) Targeted expression of A Human pituitary tumor–derived isoform of FGF Receptor–4 Recapitulates Pituitary Tumorigenesis. Journal of Clinical Investigation 109(1):69–77.
Faham, Salem et al., (1998) Diversity does make a difference: fibroblast growth factor—Heparin Interactions. Curr Opin Struct Biol 8(5):578–586.
Fingl, Edward and Woodbury, Dixon M.(1975) Chapter I: General Priciples; In: The Pharmacological Basis of Therapeutics. Fifth edition. Goodman, Louis S. and Gilman, Alfred editors. 1:1–45.
Gargiulo, B. J. et al., (2002) Phenotypic modulation of human articular chondrocytes by bistratene A. Eur Cell Mater. 3:9–18.
Givol, David and Yayon, Avner (1992) Complexity of FGF receptors: genetic basis for structural diversity and functional specificity FASEB J. 6(15):3362–3369.
Hecht, H. J. et al., (2000) Structure of fibroblast growth factor 9 shows a symmetric dimer with unique receptor–and heparin–binding interfaces. Acta Cryst. D57:378–384.
Johnson, Daniel E. and Williams, Lewis T. (1993) Structural and functional diversity in the FGF receptor multigene family. Adv Cancer Res. 60:1–41.
Kirikoshi, Hiroyuki et al., (2000) Molecular cloning and characterization of Human FGF–20 on chromosome 8p21.3–p22. Biochem Biophys Res Commun. 274(2):337–343.
Kuroda, S. et al., (1999) Anabolic effect of aminoterminally truncated Fibroblast Growth Factor 4 (FGF4) on bone. Bone 25:(4):431–437.
Nakatake, Yuhki et al., (2001) Identification of a novel fibroblast growth factor. FGF–22, preferentially expressed in the inner root sheath of the hair follicle. Biochim Biophys Acta. 1517(3):460–463.
Ngo, J. Thomas et al., (1994) Computational complexity, protein structure prediction, and the Levithal Paradox. In: The Protein Folding Problem and Tertiary Structure Prediction. K. Merz Jr. and S. Le Grand, Editors. 433–506.
Nishimura, Tetsuya et al., (2000) Identification Of a Novel FGF, FGF–21, Preferentially Expressed In The Liver. Biochim Biophys Acta 1492(1):203–206.
Okada–Ban, Mai et al., (2000) Fibroblast growth factor–2. International Journal of Biochemistry & Cell Biology 32 (3):263–267.
Olsen, Shaun K. (2003) Fibroblast growth factor (FGF) homologous factors share structural but not functional homology with FGFs J. Biol Chem. 278(36); pp. 34226–34236.
Ornitz, David M. et al., (1996) Receptor specificity of the fibroblast growth factor family. J Biol Chem. 271(25)15292–7.
Ornitz, David M. (2000) FGFs, heparan sulfate and FGFRs: Complex interactions essential for development. Bio Essays 22:108–112.
Pellegrini, Luca et al., (2000) Crystal structure of fibroblast growth factor receptor ectodomain bound to ligand and heparin. Nature 407(6807):1029–1034.
Pillai, Omathanu and Panchagnula, Ramesh (2001) Polymers in drug delivery. Curr Opin Chem Biol 5 (4):447–451.
Plotnikov, Alexander N. et al., (1999) Structural basis for FGF receptor dimerization and activation. Cell 98 (5):641–650.
Plotnikov, Alexander N. et al., (2000) Crystal structures of two FGF–FGFR complexes reveal the determinants of ligand–receptor specificity. Cell 101(4):413–424.
Sahni, Malika et al., (1999) FGF signaling inhibits chondrocyte proliferation and regulates bone development through the STAT–1 pathway. Genes Dev. 13:1361–1366.
Schlessinger, Joseph et al., (2000) Crystal structure of a ternary FGF–FGFR–1 Heparin complex reveals a dual role for heparin in FGFR binding and dimerization. Mol Cell 6(3):743–750.
Schmal, H. et al., (2007) bFGF influences human articular chondrocytes differentiation. Cytotherapy 9(2):184–93.
Seno, Masaharu et al., (1990) Carboxyl–terminal structure of basic fibroblast growth factor significantly contributes to its affinity for Heparin. Eur J Biochem. 188:239–245.
Shano; Zhang–Qiang et al., (2006) Effects of intramyocardial administration of slow–release basic fibroblast growth factor on angiogenesis and ventricular remodelling in a rat infarct model. Circ. J. 70(4):471–477.

Skolnik, Jeffrey and Fetrow, Jacquelyn S. (2000) From genes to protein structure and function: novel applications of computational approaches in the genomic era. Trends Bio Technol. 18(1):34–39.

Sleeman, Matthew et al., (2001) Identification of a new fibroblast growth factor receptor, FGFR5. Gene 271 (2):171–182.

Smith, Temple and Zhang, Xiaolin (1997) The challenges of genome sequence annotation or The devil is in the details, Nat Biotecehnol. 15(12):1222–1223.

Springer, Barry A. et al., (1994) Identification and Concerted Function of Two Receptors Binding Surfaces on Basic Fibroblast Growth Factor Required for Mitogenesis. The Journal of Biological Chemistry 269(43):26879–26884.

Stauber, Deborah J. et al., (2000) Structural interactions of fibroblast growth factor receptor with its ligands. Proc Natl Acad Sci USA 97(1):49–54.

Vajo, Zoltan et al., (2000) The Molecular and Genetic Basis of Fibroblast Growth Factor Receptor 3 Disorders: The Achondroplasia Family of Skeletal Dysplasias, Muenke Craniosynostosis, and Crouzon Syndrome with Acanthosis Nigricans. Endocrine Rev. 21(1):23–39.

Wells, James A. (1990) Additivity of mutational effects in proteins. Biochemistry 29(37):8509–8517.

Yamashita, Tetsuo et al., (2000) Identification of a novel fibroblast growth factor, FGF–23, preferentially expressed in the ventrolateral thalamic nucleus of the brain. Biochemical and Biophysical Research Communications 277 (2):494–498.

Yayon, Avner et al., (1991) Cell surface, heparin–like molecules are required for binding of basic fibroblast growth factor to its high affinity receptor. Cell 64(4):841–848.

International Search Report and Written Opinion for PCT/US2010/000108, mailed Aug. 24, 2010.

International Patent Application No. PCT/US2009/000108, filed Jan. 14, 2010, entitled "Cartilage Particle Tissue Mixtures Optionally Combined With a Cancellous Construct".

Final Office Action mailed Mar. 15, 2010 in connection with U.S. Appl. No. 10/815,778.

Final Office Action mailed Mar. 22, 2010 in connection with U.S. Appl. No. 12/010,984.

U.S. App. No. 12/881,988, filed Sep. 14, 2010.

U.S. Appl. No. 12/924,132, filed Sep. 21, 2010.

Temenoff et al., "Review: Tissue engineering for regeneration of articular cartilage", Biomaterials 21 (2000) pp. 431–440.

Hunziker, "Articular cartilage repair: are the intrinsic biological constraints undermining this processiInsuperable?", Osteoarthritis and Cartilage 7 (1999) pp. 15–28.

* cited by examiner

GLUE FOR CARTILAGE REPAIR

Matter enclosed in heavy brackets [ ] appears in the original patent but forms no part of this reissue specification; matter printed in italics indicates the additions made by reissue.

RELATED APPLICATIONS

[There is no related application.] *The instant application is a reissue of application Ser. No. 10/424,765, filed Apr. 29, 2003, and issued as U.S. Pat. No. 7,067,123.*

1. Field of Invention

The present invention is generally directed toward an implant and is more specifically directed toward a paste or gel implant material for a cartilage defect.

2. Background of the Invention

Articular cartilage injury and degeneration present medical problems to the general population which are addressed by orthopedic surgeons. Every year in the United States, over 500,000 arthroplastic or joint repair procedures are performed. These include approximately 125,000 total hip and 150,000 total knee arthroplasties and over 41,000 open arthroscopic procedures to repair cartilaginous defects of the knee.

In the knee joint, the articular cartilage tissue forms a lining which faces the joint cavity on one side and is linked to the subchondral bone plate by a narrow layer of calcified cartilage tissue on the other. Articular cartilage (hyaline cartilage) consists primarily of extracellular matrix with a sparse population of chondrocytes distributed throughout the tissue. Articular cartilage is composed of chondrocytes, type II collagen fibril network, proteoglycans and water. Active chondrocytes are unique in that they have a relatively low turnover rate and are sparsely distributed within the surrounding matrix. The collagens give the tissue its form and tensile strength and the interaction of proteoglycans with water give the tissue its stiffniess to compression, resilience and durability. The hyaline cartilage provides a low friction bearing surface over the bony parts of the joint. If the lining becomes worn or damaged resulting in lesions, joint movement may be painful or severely restricted. Whereas damaged bone typically can regenerate successfully, hyaline cartilage regeneration is quite limited because of it's limited regenerative and reparative abilities.

Articular cartilage lesions generally do not heal, or heal only partially under certain biological conditions due to the lack of nerves, blood vessels and a lymphatic system. The limited reparative capabilities of hyaline cartilage usually results in the generation of repair tissue that lacks the structure and biomechanical properties of normal cartilage. Generally, the healing of the defect results in a fibrocartilaginous repair tissue that lacks the structure and biomedical properties of hyaline cartilage and degrades over the course of time. Articular cartilage lesions are frequently associated with disability and with symptoms such as joint pain, locking phenomena and reduced or disturbed function. These lesions are difficult to treat because of the distinctive structure and function of hyaline cartilage. Such lesions are believed to progress to severe forms of osteoarthritis. Osteoarthritis is the leading cause of disability and impairment in middle-aged and older individuals, entailing significant economic, social and psychological costs. Each year, osteoarthritis accounts for as many as 39 million physician visits and more than 500,000 hospitalizations. By the year 2020, arthritis is expected to affect almost 60 million persons in the United States and to limit the activity of 11.6 million persons.

There are many current therapeutic methods being used. None of these therapies has resulted in the successful regeneration of hyaline-like tissue that withstands normal joint loading and activity over prolonged periods. Currently, the techniques most widely utilized clinically for cartilage defects and degeneration are not articular cartilage substitution procedures, but rather lavage, arthroscopic debridement, and repair stimulation. The direct transplantation of cells or tissue into a defect and the replacement of the defect with biologic or synthetic substitutions presently accounts for only a small percentage of surgical interventions. The optimum surgical goal is to replace the defects with cartilage-like substitutes so as to provide pain relief, reduce effusions and inflammation, restore function, reduce disability and postpone or alleviate the need for prosthetic replacement.

Lavage and arthroscopic debridement involve irrigation of the joint with solutions of sodium chloride, Ringer or Ringer and lactate. The temporary pain relief is believed to result from removing degenerative cartilage debris, proteolytic enzymes and inflammatory mediators. These techniques provide temporary pain relief, but have little or no potential for further healing.

Repair stimulation is conducted by means of drilling, abrasion arthroplasty or microfracture. Penetration into the subchondral bone induces bleeding and fibrin clot formation which promotes initial repair, however, the tissue formed is fibrous in nature and not durable. Pain relief is temporary as the tissue exhibits degeneration, loss of resilience, stiffness and wear characteristics over time.

The periosteum and perichondrium have been shown to contain mesenchymal progenitor cells capable of differentiation and proliferation. They have been used as grafts in both animal and human models to repair articular defects. Few patients over 40 years of age have obtained good clinical results, which most likely reflects the decreasing population of osteochondral progenitor cells with increasing age. There have also been problems with adhesion and stability of the grafts, which result in their displacement or loss from the repair site.

Transplantation of cells grown in culture provides another method of introducing a new cell population into chondral and osteochondral defects. Carticel® is a commercial process to culture a patient's own cartilage cells for use in the repair of cartilage defects in the femoral condyle marketed by Genzyme Biosurgery in the United States and Europe. The procedure uses arthroscopy to take a biopsy from a healthy, less loaded area of articular cartilage. Enzymatic digestion of the harvested tissue releases the cells that are sent to a laboratory where they are grown for a period ranging from 2–5 weeks. Once cultivated, the cells are injected during a more open and extensive knee procedure into areas of defective cartilage where it is hoped that they will facilitate the repair of damaged tissue. An autologous periosteal flap with cambium layer is used to seal the transplanted cells in place and act as a mechanical barrier. Fibrin glue is used to seal the edges of the flap. This technique preserves the subchondral bone plate and has reported a high success rate. Proponents of this procedure report that it produces satisfactory results, including the ability to return to demanding physical activities, in more than 90% of patients and that biopsy specimens of the tissue in the graft sites show hyaline-like cartilage repair. More work is needed to assess the function and durability of the new tissue and determine whether it improves joint function and delays or prevents joint degeneration. As with the perichondrial graft, patient/donor age may compromise the success of this procedure as chondrocyte population decreases with increasing age. Disadvantages to this procedure include the need for two separate surgical procedures, potential damage to surrounding cartilage when the periosteal patch is sutured in place, the requirement of demanding microsurgical techniques, and the expensive cost of the procedure which is currently not covered by insurance.

Osteochondral transplantation or mosaicplasty involves excising all injured or unstable tissue from the articular defect and creating cylindrical holes in the base of the defect and underlying bone. These holes are filled with autologous cylindrical plugs of healthy cartilage and bone in a mosaic fashion. The osteochondral plugs are harvested from a lower weight-bearing area of lesser importance in the same joint. This technique, shown in Prior Art FIG. 2, can be performed as arthroscopic or open procedures. Reports of results of osteochondral plug autografts in a small number of patients indicate that they decrease pain and improve joint function, however, long-term results have not been reported. Factors that can compromise the results include donor site morbidity, effects of joint incongruity on the opposing surface of the donor site, damage to the chondrocytes at the articular margins of the donor and recipient sites during preparation and implantation, and collapse or settling of the graft over time. The limited availability of sites for harvest of osteochondral autografts restricts the use of this approach to treatment of relatively small articular defects and the healing of the chondral portion of the autograft to the adjacent articular cartilage remains a concern.

Transplantation of large allografts of bone and overlying articular cartilage is another treatment option that involves a greater area than is suitable for autologous cylindrical plugs, as well as for a non-contained defect. The advantages of osteochondral allografts are the potential to restore the anatomic contour of the joint, lack of morbidity related to graft harvesting, greater availability than autografts and the ability to prepare allografts in any size to reconstruct large defects. Clinical experience with fresh and frozen osteochondral allografts shows that these grafts can decrease joint pain, and that the osseous portion of an allograft can heal to the host bone and the chondral portion can function as an articular surface. Drawbacks associated with this methodology in the clinical situation include the scarcity of fresh donor material and problems connected with the handling and storage of frozen tissue. Fresh allografts carry the risk of immune response or disease transmission. Musculoskeletal Transplant Foundation (MTF) has preserved fresh allografts in a media that maintains a cell viability of 50% for 35 days for use as implants. Frozen allografts lack cell viability and have shown a decreased amount of proteoglycan content which contribute to deterioration of the tissue.

A number of patents in the prior art show the use of bone putty, pastes or gels to fill bone defects. U.S. Pat. No. 5,290,558 issued Mar. 1, 1994 discloses a flowable demineralized bone powder composition using an osteogenic bone powder with large particle size ranging from about 0.1 to about 1.2 cm. mixed with a low molecular weight polyhydroxy compound possessing from 2 to about 18 carbons including a number of classes of different compounds such as monosaccharides, disaccharides, water dispersible oligosaccharides and polysaccharides.

A bone gel is disclosed in the U.S. Pat. No. 5,073,373 issued Dec. 17, 1991. Bone lamellae in the shape of threads or filaments retaining low molecular weight glycerol carrier are disclosed in U.S. Pat. Nos. 5,314,476 issued May 24, 1994 and 5,507,813 issued Apr. 16, 1996 and the tissue forms described in these patents are known commercially as the GRAFTON® Putty and Flex, respectively.

U.S. Pat. No. 5,356,629 issued Oct. 18, 1994 discloses making a rigid gel in the nature of a bone cement to fill defects in bone by mixing biocompatible particles, preferably polymethylmethacrylate coated with polyhydroxyethylmethacrylate in a matrix selected from a group which lists hyaluronic acid to obtain a molded semi-solid mass which can be suitably worked for implantation into bone. The hyaluronic acid can also be utilized in monomelic form or in polymeric form preferably having a molecular weight not greater than about one million Daltons. It is noted that the nonbioabsorbable material which can be used to form the biocompatible particles can be derived from xenograft bone, homologous bone, autogenous bone as well as other materials. The bioactive substance can also be an osteogenic agent such as demineralized bone powder, morselized cancellous bone, aspirated bone marrow and other autogenous bone sources. The average size of the particles employed is preferably about 0.1 to about 3.0 mm, more preferably about 0.2 to about 1.5 mm, and most preferably about 0.3 to about 1.0 mm. It is inferentially mentioned but not taught that particles having average sizes of about 7,000 to 8,000 microns, or even as small as about 100 to 700 microns can be used.

U.S. Pat. No. 4,172,128 issued Oct. 23, 1979 discloses a demineralized bone material mixed with a carrier to reconstruct tooth or bone material by adding a mucopolysaccharide to a mineralized bone colloidal material. The composition is formed from a demineralized coarsely ground bone material, which may be derived from human bones and teeth, dissolved in a solvent forming a colloidal solution to which is added a physiologically inert polyhydroxy compound such as mucopolysaccharide or polyuronic acid in an amount which causes orientation when hydrogen ions or polyvalent metal ions are added to form a gel. The gel will be flowable at elevated temperatures above 35° C. and will solidify when brought down to body temperature. Example 25 of the patent notes that mucopolysaccharides produce pronounced ionotropic effects and that hyaluronic acid is particularly responsible for spatial cross-linking.

U.S. Pat. No. 6,030,635 issued Feb. 29, 2000 and U.S. Pat. No. 6,437,018 issued Aug. 20, 2002 are directed toward a malleable bone putty and a flowable gel composition for application to a bone defect site to promote new bone growth at the site which utilize a new bone growth inducing compound of demineralized lyophilized allograft bone powder. The bone powder has a particle size ranging from about 100 to about 850 microns and is mixed in a high molecular weight hydrogel carrier which contains a sodium phosphate saline buffer.

The use of implants for cartilage defects is much more limited. Aside from the fresh allograft implants and autologous implants, U.S. Pat. No. 6,110,209 issued Nov. 5, 1998 shows the use an autologous articular cartilage cancerous bone paste to fill arthritic defects. The surgical technique is arthroscopic and includes debriding (shaving away loose or fragmented articular cartilage), followed by morselizing the base of the arthritic defect with an awl until bleeding occurs. An osteochondral graft is then harvested from the inner rim of the intercondylar notch using a trephine. The graft is then morselized in a bone graft crusher, mixing the articular cartilage with the cancellous bone. The paste is then pushed into the defect and secured by the adhesive properties of the bleeding bone. The paste can also be mixed with a cartilage stimulating factor, a plurality of cells, or a biological glue. All patients are kept non-weight bearing for four weeks and used a continuous passive motion machine for six hours each night. Histologic appearance of the biopsies have mainly shown a mixture of fibrocartilage with hyaline cartilage.

Concerns associated with this method are harvest site morbidity and availability, similar to the mosaicplasty method. cl

SUMMARY OF THE INVENTION

A cartilage implant material in paste or gel form for repairing articular cartilage defects is composed of milled allograft cartilage pieces in a bioabsorbable carrier. Autologous chondrocyte in an amount exceeding the number naturally occurring in hyaline cartilage for a mature adult between 20 and 55 years of age may also be applied to the matrix. Additives may be applied to the mixture in order to increase chondrocyte migration and proliferation. The implant material can support the addition of a variety of chondrogenic stimulating factors including, but not limited to growth factors (FGF-2, FGF-5, IGF-1, TGF-β, BMP-2, BMP-7, PDGF, VEGF), human allogenic or autologous chondrocytes, human allogenic or autologous bone marrow cells, stem cells, demineralized bone matrix, insulin, insulin-like growth factor-1, transforming growth factor-B, interleukin-1 receptor antagonist, hepatocyte growth factor, platelet-derived growth factor, Indian hedgehog and parathyroid hormone-related peptide or bioactive glue.

The implant material is placed in the lesion area and may be sealed with a periosteum cap.

It is an object of the invention to provide an allograft implant material for joints which provides pain relief, restores normal function and will postpone or alleviate the need for prosthetic replacement.

It is also an object of the invention to provide a cartilage repair implant material which is easily placed in a defect area by the surgeon using an arthroscopic, minimally invasive technique.

It is further an object of the invention to provide an allograft implant material procedure which is applicable for both partial and full thickness lesions.

It is yet another object of the invention to provide an allograft implant material which facilitates growth of hyaline cartilage.

It is an additional object of the invention to provide implant paste and gel material formulations that satisfy surgical requirements and are made from donated human available allograft tissue, some of which would otherwise be considered waste and thrown away.

These and other objects, advantages, and novel features of the present invention will become apparent when considered with the teachings contained in the detailed disclosure along with the accompanying drawings.

DESCRIPTION OF THE INVENTION

The terms "tissue" is used in the general sense herein to mean any transplantable or implantable tissue, the survivability of which is improved by the methods described herein upon implantation. In particular, the overall durability and longevity of the implant are improved, and host-immune system mediated responses, are substantially eliminated.

The terms "transplant" and "implant" are used interchangably to refer to tissue, material or cells (xenogeneic or allogeneic) which may be introduced into the body of a patient to replace or supplement the structure or function of the endogenous tissue.

The terms "autologous" and "autograft" refer to tissue or cells which originate with or are derived from the recipient, whereas the terms "allogeneic" and "allograft" refer to cells and tissue which originate with or are derived from a donor of the same species as the recipient. The terms "xenogeneic" and "xenograft" refer to cells or tissue which originates with or is derived from a species other than that of the recipient.

The term "gel" refers to a mixture of minced or milled pretreated allograft cartilage in a biocomposite carrier having a viscosity which is less than and is less rigid than a mixture of minced or milled pretreated allograft cartilage in a biocompatible carrier referred to by the terms "putty" or "paste" and contains less cartilage by weight than putty or paste.

Figure 1:
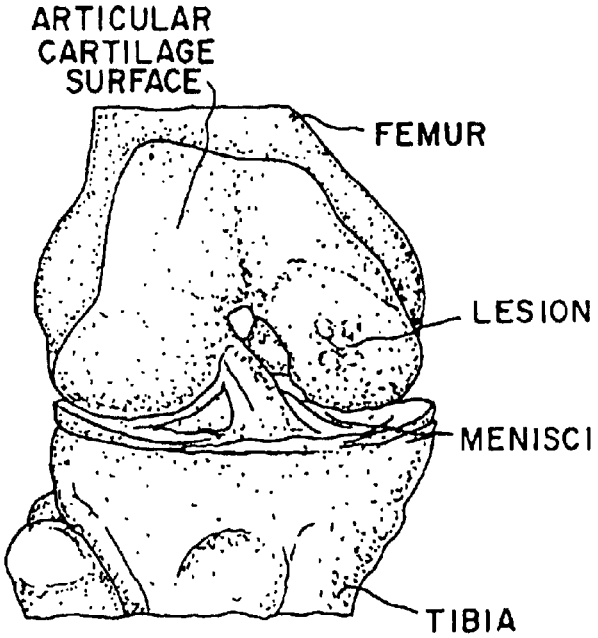
FIG. 1 shows the anatomy of a knee joint with a lesion.
Figure 2:
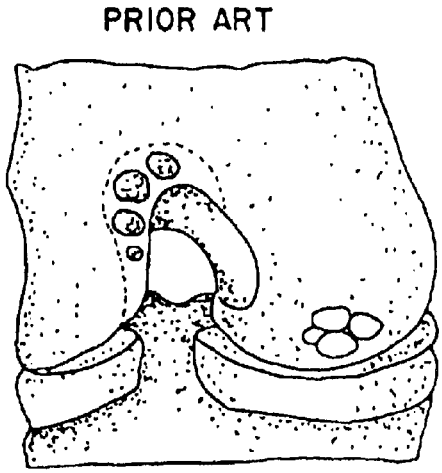
FIG. 2 shows a schematic mosaicplasty as known in the prior art.
Figure 3:
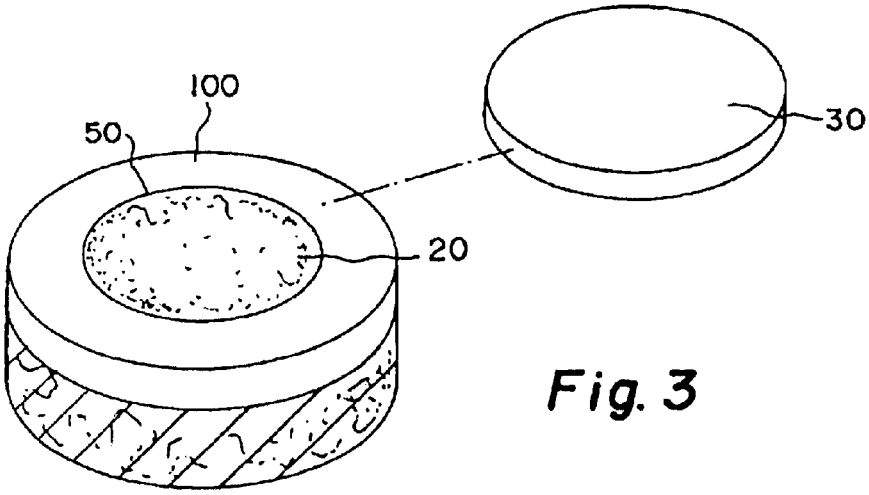
FIG. 3 shows a schematic perspective view of cartilage defect material placed in a defect site with an exploded periosteum cap.

The present invention is directed towards a cartilage repair material and method of treatment. The preferred embodiment and best mode of the invention is shown in FIG. 3. In the production of the invention, allograft hyaline cartilage is lyophilized reducing its water content and milled for ease in application.

After washes with sterile de-ionized (DI) water, the cartilage material was frozen at −20° to −100° C. preferably −70° C. and lyophilized to reduce the water content within the range of about 0.1% to about 8.0%. The cartilage is frozen with liquid nitrogen and ground into particles.

A lesion or defect is removed by cutting a bore 50 or trimming a lesion in the implant area 100 and filling the bore 50 or lesion area with a milled cartilage mixture 20 of paste or gel consisting together with a biological carrier such as hyaluronic acid and its derivatives, gelatin, collagen, chitosan, alginate, buffered PBS, Dextran, or polymers and one or more additives namely chondrogenic stimulating factors including, but not limited to growth factors (FGF-2, FGF-5, IGF-1, TGF-β, BMP-2, BMP-7, PDGF, VEGF), human allogenic or autologous chondrocytes, human allogenic cells, human allogenic or autologous bone marrow cells, human allogenic or autologous stem cells, demineralized bone matrix, insulin, insulin-like growth factor-1, interleukin-1 receptor antagonist, hepatocyte growth factor, platelet-derived growth factor, Indian hedgehog and parathyroid hormone-related peptide.

Suitable organic glue material can be used to keep the viscous cartilage mixture 20 fixed in place in the implant area or to affix a periosteal cap 30 in place over the surrounding hyaline cartilage area 100. Suitable organic glue material can be found commercially, such as for example; TISSEEL® or TISSUCOL®) (fibrin based adhesive; Immuno AG, Austria), Adhesive Protein (Sigma Chemical, USA), and Dow Corning Medical Adhesive B (Dow Corning, USA).

EXAMPLE 1

A matrix of minced cartilage putty consisting of minced or milled allograft articular cartilage which has been lyophilized so that its water content ranges from 0.1% to 8.0% with a cartilage content ranging from 25% to 50% by weight is mixed with a carrier of sodium hyaluronate solution (HA) (molecular weight ranging from $7.0\times10^5$ to $1.2\times10^6$) or any other bioabsorbable carrier such as hyaluronic acid and its derivatives, gelatin, collagen, chitosan, alginate, buffered PBS, Dextran, or polymers, the carrier ranging from 75% to 50% by weight. The cartilage is milled to a size ranging from 0.01 mm to 1 mm. In gel form, the minced cartilage which has been lyophilized so that its water content ranges from 0.1% to 8.0% ranging from 15% to 30% by weight and the carrier ranges from 85% to 70% by weight. The particle size of the cartilage when milled is less than or equal to 1 mm dry in the previously stated range. The cartilage pieces can be processed to varying particle sizes and the HA or other carrier can have different viscosities depending on the desired consistency of the putty or paste. This cartilage matrix can be deposited into the cartilage defect arthroscopically and fit into the defect where it is held in place by it's own viscosity, mixed with fibrin glue or covered with a periosteal or perichondrial flap, then sealed with biological glue. As with the first two matrices, this matrix can support the previously mentioned chondrogenic factors.

EXAMPLE 2

A matrix of minced cartilage putty consisting of minced or milled allograft cartilage which has been lyophilized so that its water content ranges from 0.1% to 8.0% ranging from 25% to 50% by weight is mixed with a carrier of sodium hyaluronate solution (HA) ($7.0\times10^5$ to $1.2\times10^6$) or any other bioabsorbable carrier such as hyaluronic acid and its derivatives, gelatin, collagen, chitosan, alginate, buffered PBS, Dextran, or polymers ranging from 75% to 50% by weight. In a gel form, the minced cartilage which has been lyophilized so that its water content ranges from 0.01% to 8.0% ranging from 15% to 30% by weight and the carrier ranges from 85% to 70% by weight. The particle size of the cartilage is less than or equal to 1 mm dry ranging from 0.01 mm to 1 mm. The cartilage pieces can be processed to varying particle sizes and the HA or carrier can have different viscosities depending on the desired consistency of the putty or paste. Autologous or allogenic cells which have been grown outside the patient are inserted by syringe into the matrix before, during or after deposit of the cartilage matrix into the defect area. Such cells include allogenic or autologous bone marrow cells, stem cells and chondrocyte cells. The cellular density of the cells preferably ranges from about $1\times10^8$ to $5\times10^8$ or from about 100 million to about 500 million cells per cc of putty or gel mixture. This composite material can be injected into the cartilage defect arthroscopically and fit into the defect where it is held in place by it's own viscosity, or covered with a periosteal or perichondrial flap, then sealed with biological glue. As with the first matrix, this matrix can support the previously mentioned chondrogenic factors.

The operation of placing the cartilage composition in a cartilage defect, comprises (a) cutting a patient's tissue at a site of a cartilage defect to remove the diseased area of cartilage; (b) placing a mixture of milled allograft cartilage in a bioabsorbable carrier in the defect area; and (c) placing a periosteal cover over the mixture of the inserted milled allograft cartilage in a bioabsorbable carrier to contain the mixture in the defect area for a predetermined period of time to promote cartilage growth at the defect site. Alternate steps include the addition of growth factors, chondrocytes, bone marrow cells and stem cells.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive.

What we claim is:

1. A [sterile allograft] cartilage defect [implant] *repair* material for use in human beings, comprising *a mixture including lyophilized, freeze*-milled allograft cartilage pieces [sized less] *having a size not greater* than 1 mm and *a bioabsorbable carrier, said cartilage pieces being formed from allograft cartilage that has been* lyophilized so [that their] *as to reduce its* water content [ranges from] *to an amount within the range of from* about 0.1% to about 8.0% [in a bioabsorbable carrier] *by weight*.

[2. A sterile allograft cartilage defect implant material as claimed in claim 1 wherein said milled cartilage ranges from about 25% to about 50% by weight and said carrier ranges from about 75% to about 50% by weight.]

[3. A sterile allograft cartilage defect implant material as claimed in claim 1 wherein said milled cartilage ranges from about 15% to about 30% by weight with the carrier ranging from about 85% to about 70% by weight.]

4. A [sterile allograft] cartilage defect [implant] *repair* material as claimed in claim 1, wherein said *bioabsorbable* carrier is *selected from the group consisting of* sodium hyaluronate and [its derivatives] hyaluronic acid.

5. A [sterile allograft] cartilage defect [implant] *repair* material as claimed in claim 1, wherein said [implant material] *mixture* includes a protein glue.

6. A [sterile allograft] cartilage defect [implant] *repair* material as claimed in claim 1, wherein said [implant material] *mixture* includes [the addition of] autologous chondrocytes [to achieve a concentration exceeding the concentration of chondrocytes naturally occurring in the patient] *at a concentration greater than the concentration of chondrocytes that are naturally present in hyaline cartilage of a human being having an age in the range of from 20 years to 55 years*.

7. A [sterile allograft] cartilage defect [implant] *repair* material as claimed in claim 1, wherein said [milled] *allograft* cartilage [is] *pieces include* hyaline cartilage.

8. A [sterile allograft] cartilage defect [implant] *repair* material as claimed in claim 1, wherein said [milled] *allograft* cartilage [is fibrosus cartilage] *pieces include fibrocartilage*.

9. A [sterile allograft] cartilage defect [implant] *repair* material as claimed in claim 1, wherein said [milled] *allograft* cartilage [is] *pieces include* hyaline and [fibrosus cartilage] *fibrocartilage*.

10. A [sterile allograft] cartilage defect [implant] *repair* material *as* claimed in claim 1, [including] *wherein said mixture includes* an additive [to said implant material consisting of one or more of a] *selected from the* group consisting of *a* growth [factors] *factor*, human allogenic cells, human allogenic bone marrow cells, human autologous bone marrow cells, human allogenic stem cells, human autologous stem cells, *a* human demineralized bone matrix, [and] insulin, *insulin-like growth factor-1, an interleukin-1, receptor agonist, a hepatocyte growth factor, a platelet-derived growth factor, Indian hedgehog, and a parathryroid hormone-related peptide*.

11. A [sterile] cartilage *defect* repair material as claimed in claim 10, wherein said growth [factors are one or more of a] *factor is selected from the* group consisting of FGF-2, FGF-5, IGF-1, TGF-β, BMP-2, BMP-7, PDGF, *and* VEGF.

12. A [sterile allograft] cartilage defect [implant] *repair* material as claimed in claim 1, wherein said *bioabsorbable* carrier [comprises one or more bioabsorbable carriers taken] *is selected* from [a] *the* group consisting of sodium hyaluronate, hyaluronic acid [and its derivatives], gelatin, collagen, chitosan, alginate, buffered PBS, Dextran, [or] *and* polymers.

13. A [sterile allograft] cartilage defect [implant] *repair* material *for use in human beings,* comprising *a mixture*

*including lyophilized, freeze*-milled allograft articular cartilage pieces ranging from 0.01 mm to 1.0 mm in size [in], a bioabsorbable carrier [taken] *selected* from [a] *the* group consisting of sodium hyaluronate, *hyaluronic acid,* gelatin, collagen, chitosan, alginate, buffered PBS, Dextran, [or] *and* polymers, and allogenic chondrocytes [in an amount exceeding the natural occurrence of same in articular cartilage] *at a concentration greater than the concentration of chondrocytes that are naturally present in hyaline cartilage of a human being having an age in the range of from 20 years and 55 years*.

14. A [sterile] cartilage defect [implant] *repair* material as claimed in claim 13, wherein said allograft articular cartilage [is] *pieces include* hyaline cartilage.

15. A [sterile allograft] cartilage defect [implant] *repair* material as claimed in claim 13, wherein said [milled] *allograft articular* cartilage [is fibrous cartilage] *pieces include fibrocartilage*.

16. A [sterile allograft] cartilage defect [implant] *repair* material as claimed in claim 13, wherein said [milled] *allograft articular* cartilage [is] *pieces include* hyaline *cartilage* and [fibrous cartilage] *fibrocartilage*.

17. A [sterile] cartilage *defect* repair material as claimed in claim 13 [wherein said implant material includes], *further comprising* an additive [consisting of one or more of a] *selected from the* group consisting of *a* growth [factors] *factor*, human allogenic cells, human allogenic bone marrow cells, human autologous bone marrow cells, human allogenic stem cells, human autologous stem cells, demineralized bone matrix, [and] insulin, *insulin-like growth factor-1, interleukin-1 receptor agonist, hepatocyte growth factor, platelet-derived growth factor, Indian hedgehog, and parathyroid hormone-related peptide*.

18. A [sterile] cartilage *defect* repair material as claimed in claim 17, wherein said growth [factors are one or more of a] *factor is selected from the* group consisting of FGF-2, FGF-5, IGF-1, TGF-β, BMP-2, BMP-7, PDGF, *and* VEGF.

[19. A sterile cartilage defect implant material as claimed in claim 13 wherein said milled cartilage ranges from about 25% to about 50% by weight and said carrier ranges from about 75% to about 50% by weight.]

[20. A sterile cartilage defect implant material as claimed in claim 13 wherein said milled cartilage ranges from about 15% to about 30% by weight with the carrier ranging from about 85% to about 70% by weight.]

21. A [sterile allograft] cartilage defect [implant] *repair* material *for use in human beings,* comprising lyophilized, *freeze*-milled allograft articular cartilage pieces ranging from 0.01 mm to 1.0 mm in size [in], a bioabsorbable carrier [taken] *selected* from [a] *the* group consisting of sodium hyaluronate, hyaluronic acid [and its derivatives], gelatin, collagen, chitosan, alginate, buffered PBS, Dextran [or], *and* polymers, and autologous bone marrow cells [in an amount exceeding the natural occurrence of same in a patient being treated] *at a concentration greater than the concentration of bone marrow cells that are naturally present in hyaline cartilage of a human being having an age in the range of from 20 years to 55 years*.

22. A [sterile] cartilage defect repair material as claimed in claim 21 [including], *further comprising* an additive [in said implant material which consists of one or more of a] *selected from the* group consisting of *a* growth [factors] *factor*, human allogenic cells, autologous chondrocytes, demineralized bone matrix, [and] insulin, *insulin-like growth factor-1, an interleukin-1 receptor agonist, a hepatocyte growth factor, a platelet-derived growth factor, Indian hedgehog, and a parathyroid hormone-related peptide*.

23. A [sterile] cartilage *defect* repair material as claimed in claim 22, wherein said growth [factors are one or more of a] *factor is selected from the* group consisting of FGF-2, FGF-5, IGF-1, TGF-β, BMP-2, BMP-7, PDGF, *and* VEGF.

24. A [sterile allograft] cartilage defect [implant] *repair* material as claimed in claim 21, wherein said bioabsorbable carrier [consists] *is selected from the group consisting* of sodium hyaluronate[,] *and* hyaluronic acid [and its derivatives].

25. A [sterile] cartilage defect *repair* material as claimed in claim 21; wherein said [lyophilized] *allograft articular* cartilage pieces [have ranging from] *are formed from allograft articular cartilage that has been lyophilized so as to reduce its water content to the range of* about 0.1% to *about* 8.0%.

26. A [sterile allograft] cartilage defect [implant] *repair* material as claimed in claim 21, wherein said allograft articular cartilage [is] *pieces include* hyaline cartilage.

27. A [sterile allograft] cartilage defect [implant] *repair* material as claimed in claim 21, wherein said [milled] *allograft articular* cartilage [is fibrous cartilage] *pieces include fibrocartilage*.

28. A [sterile allograft] cartilage defect [implant] *repair* material as claimed in claim 21, wherein said [milled] *allograft articular* cartilage [is] *pieces include* hyaline *cartilage* and [fibrous cartilage] *fibrocartilage*.

29. A [sterile allograft] cartilage defect [implant] *repair* material as claimed in claim 21, wherein said [milled] *allograft articular* cartilage [ranges] *pieces are present in said material at an amount in the range of* from about 25% to about 50% by weight and said *bioabsorbable* carrier [ranges] *is present in said material at an amount in the range of* from about [75%] *50%* to about [50%] *75%* by weight.

30. A [sterile allograft] cartilage defect [implant] *repair* material as claimed in claim 21, wherein said [milled] *allograft articular* cartilage [ranges] *pieces are present in said material in an amount in the range of* from about 15% to about 30% by weight [with the] *and said bioabsorbable* carrier [ranging] *is present in said material in an amount in the range of* from about [85%] *70%* to about [70%] *85%* by weight.

[31. A sterile cartilage defect implant material comprising lyophilized milled allograft articular cartilage pieces ranging from 0.01 mm to 1.0 mm in size in a bioabsorbable carrier taken from a group consisting of sodium hyaluronate, hyaluronic acid and its derivatives, gelatin, collagen, chitosan, alginate, buffered PBS, Dextran or polymers and autologous stem cells in an amount exceeding the natural occurrence of same in a patient being treated.]

32. A method of placing a cartilage defect *repair* material in a cartilage defect *site in a human being*, [said] *the* cartilage [defect] *repair* material [comprising] *having a mixture including lyophilized freeze*-milled allograft articular cartilage [which has been lyophilized and mixed in] *pieces and* a bioabsorbable carrier, *said method* comprising the steps of:

(a) cutting a patient's tissue [at a site of a cartilage defect] to remove [a] diseased [area of] cartilage *from the cartilage defect site*;

(b) adding [autologous] cells to [said] *the* mixture [of milled allograft cartilage in a bioabsorbable carrier];

(c) placing [a] *the* mixture [of milled allograft cartilage] with *the* added [autologous] cells [in a bioabsorbable carrier in] *into* the cartilage defect [area where cartilage has been removed] *site*; and (d) placing a cover over the mixture [of milled allograft cartilage in a bioabsorbable carrier] *and the added cells so as* to contain the mixture *and the added cells* in *the* cartilage defect site [for a predetermined period of time].

33. The method of claim 32, [wherein] *further comprising the step of adding* growth factors [are added] to [said] *the* mixture.

34. The method of claim 32, wherein said [autologous] cells [are] *include* chondrocytes.

35. The method of claim 32, wherein said [autologous] cells [are] *include* bone marrow cells.

36. The method of claim 32, wherein said [autologous] cells [are] *include* stem cells.

37. A [sterile allograft] cartilage defect [implant] *repair* material *for use in a human being,* comprising *a mixture including* lyophilized, *freeze*-milled allograft articular cartilage pieces ranging from 0.01 mm to 1.0 mm in size [in], a bioabsorbable carrier [taken] *selected* from [a] *the* group consisting of sodium hyaluronate, hyaluronic acid [and its derivatives], and chitosan, and autologous chondrocytes [in an amount exceeding the natural occurrence of same in articular cartilage] *at a concentration greater than the concentration of chondrocytes that are naturally present in hyaline cartilage of a human being having an age in the range of from 20 years and 55 years,* wherein said [milled] *allograft articular* cartilage [ranges] *pieces are present in said mixture at an amount within the range of* from about 25% to about 50% by weight and said bioabsorbable carrier [ranges] *is present in said mixture at an amount within the range of* from about [75%] *50%* to about [50%] *75%* by weight.

38. A [sterile allograft] cartilage defect [implant] *repair* material *for use in a human being,* comprising *a mixture including* lyophilized, *freeze*-milled allograft articular cartilage pieces ranging from 0.01 mm to 1.0 mm in size [in], a bioabsorbable carrier [taken] *selected* from [a] *the* group consisting of gelatin, collagen, and alginate, and autologous chondrocytes [in an amount exceeding the natural occurrence of same in articular cartilage] *at a concentration greater than the concentration of chondrocytes that are naturally present in hyaline cartilage of a human being having an age in the range of from 20 years and 55 years,* wherein said [milled] *allograft articular* cartilage [ranges] *pieces are present in said mixture at an amount within the range of* from about 25% to about 50% by weight and said bioabsorbable carrier [ranges] *is present in said mixture at an amount within the range of* from about [75%] *50%* to about [50%] *75%* by weight.

39. A [sterile allograft] cartilage defect [implant] *repair* material *for use in a human being,* comprising *a mixture including* lyophilized, *freeze*-milled allograft articular cartilage pieces ranging from 0.01 mm to 1.0 mm in size [in], a bioabsorbable carrier [taken] *selected* from [a] *the* group consisting of buffered PBS, Dextran [or], *and* polymers, and autologous chondrocytes [in an amount exceeding the natural occurrence of same in articular cartilage] *at a concentration greater than the concentration of chondrocytes that are naturally present in hyaline cartilage of a human being having an age in the range of from 20 years and 55 years,* wherein said [milled] *allograft articular* cartilage [ranges] *pieces are present in said mixture at an amount within the range of* from about 25% to about 50% by weight and said bioabsorbable carrier [ranges] *is present in said mixture at an amount within the range of* from about [75%] *50%* to about [50%] *75%* by weight.

*40. A cartilage defect repair material as claimed in claim 1, wherein said cartilage pieces are present in said mixture at an amount within the range of from about 25% to about 50% by weight, and said bioabsorbable carrier is present in said mixture at an amount within the range of from about 50% to about 75% by weight.*

*41. A cartilage defect repair material as claimed in claim 1, wherein said cartilage pieces are present in said mixture at an amount within the range of from about 15% to about 30% by weight, and said bioabsorbable carrier is present in said mixture at an amount within the range of from about 70% to about 85% by weight.*

*42. A cartilage defect repair material as claimed in claim 1, wherein said lyophilized. freeze-milled allograft cartilage pieces lack cell viability.*

*43. A cartilage defect repair material as claimed in claim 1, wherein said cartilage defect repair material is free of bone pieces.*

*44. A cartilage defect repair material as claimed in claim 1, wherein said lyophilized, freeze-milled allograft cartilage pieces are formed by a process including the steps of harvesting a donor tissue consisting essentially of articular cartilage, lyophilizing said donor tissue, and freeze-milling said donor tissue.*

*45. A cartilage defect repair material as claimed in claim 1, wherein said lyophilized, freeze-milled allograft cartilage pieces are formed by milling frozen allograft articular cartilage.*

*46. A cartilage defect repair material as claimed in claim 1, wherein said lyophilized, freeze-milled cartilage pieces are formed by freezing allograft cartilage with liquid nitrogen and milling the frozen cartilage.*

*47. A cartilage defect repair material as claimed in claim 1, wherein said cartilage defect repair material is free of added chondrocytes.*

*48. A cartilage defect repair material as claimed in claim 1, wherein said lyophilized, freeze-milled allograft cartilage pieces have an ability to promote the growth of new articular cartilage in the cartilage defect.*

*49. A cartilage defect repair material as claimed in claim 13, wherein said mixture includes a protein glue.*

*50. A cartilage defect repair material as claimed in claim 13, wherein said allograft articular cartilage pieces are formed from allograft articular cartilage that has been lyophilized so as to reduce its water content to the range of from about 0.1% to about 8.0% by weight.*

*51. A cartilage defect repair material as claimed in claim 13, wherein said cartilage pieces are present in said mixture at an amount within the range of from about 25% to about 50% by weight, and said bioabsorbable carrier is present in said mixture at an amount within the range of from about 50% to about 75% by weight.*

*52. A cartilage defect repair material as claimed in claim 13, wherein said cartilage pieces are present in said mixture at an amount within the range of from about 15% to about 30% by weight, and said bioabsorbable carrier is present in said mixture at an amount within the range of from about 70% to about 85% by weight.*

*53. A cartilage defect repair material as claimed in claim 21, further comprising a protein glue.*

*54. The method of claim 32, further comprising the step of fixing the mixture in the cartilage defect site with an organic glue.*

*55. The method of claim 32, further comprising the step of keeping the cover over the mixture for a predetermined period of time that is sufficient to promote cartilage growth at the cartilage defect site.*

*56. The method of claim 32, wherein said cover is a periosteal flap.*

*57. The method of claim 32, wherein said cover is a perichondrial flap.*

*58. The method of claim 32, wherein, in said step (b), the cells are selected from the group consisting of chondrocytes, bone marrow cells and stem cells, and the cells are added so as to achieve a concentration greater than the concentration*

*of corresponding cells that are naturally present in hyaline cartilage of a human being having an age in the range of from 20 years and 55 years.*

*59. A cartilage defect repair material for use in human beings, comprising lyophilized, freeze-milled allograft cartilage pieces having a size not greater than 1 mm, wherein said cartilage pieces are included in a mixture that also includes a bioabsorbable carrier, said cartilage pieces being present in said mixture at an amount within the range of from about 25% to about 50% by weight, and said bioabsorbable carrier being present in said mixture at an amount within the range of from about 50% to about 75% by weight.*

*60. A cartilage defect repair material as claimed in claim 59, wherein said cartilage pieces are formed from allograft cartilage that has been lyophilized so as to reduce its water content to an amount within the range of from about 0.1% to about 8.0% by weight.*

*61. A cartilage defect repair material as claimed in claim 59, wherein said size ranges from 0.01 mm to 1.0 mm.*

*62. A cartilage defect repair material as claimed in claim 59, wherein said material is free of added chondrocytes.*

*63. A cartilage defect repair material as claimed in claim 59, wherein said cartilage pieces are formed by freezing allograft cartilage with liquid nitrogen and milling the frozen cartilage.*

*64. A cartilage defect repair material as claimed in claim 59, wherein said cartilage pieces are formed by freeze-milling allograft cartilage subsequent to lyophilization.*

*65. A cartilage defect repair material for use in human beings, comprising lyophilized, freeze-milled allograft cartilage pieces having a size not greater than 1 mm, wherein said cartilage pieces are included in a mixture that also includes a bioabsorbable carrier, said cartilage pieces being present in said mixture at an amount within the range of from about 15% to about 30% by weight, and said bioabsorbable carrier being present in said mixture at an amount within the range of from about 70% to about 85% by weight.*

*66. A cartilage defect repair material as claimed in claim 65, wherein said cartilage pieces are formed from allograft cartilage that has been lyophilized so as to reduce its water content to an amount within the range of from about 0.1% to about 8.0% by weight.*

*67. A cartilage defect repair material as claimed in claim 65, wherein said size ranges from 0.01 mm to 1.0 mm.*

*68. A cartilage defect repair material as claimed in claim 65, wherein said material is free of added chondrocytes.*

*69. A cartilage defect repair material as claimed in claim 65, wherein said cartilage pieces are formed by freezing allograft cartilage with liquid nitrogen and milling the frozen cartilage.*

*70. A cartilage defect repair material as claimed in claim 65, wherein said cartilage pieces are formed by freeze-milling allograft cartilage subsequent to lyophilization.*

*71. A method of repairing a cartilage defect in a human being, comprising the step of placing in a defect site lyophilized, freeze-milled allograft cartilage pieces having a size not greater than 1 mm.*

*72. A method as claimed in claim 71, wherein the cartilage pieces have a water content ranging from about 0.1% to about 8.0% by weight prior to their placement in the defect site.*

*73. A method as claimed in claim 71, wherein the cartilage pieces are formed from allograft cartilage which has been lyophilized so as to reduce its water content to an amount within the range of from about 0.1% to about 8.0% by weight.*

*74. A method as claimed in claim 71, wherein the size ranges from 0.01 mm to 1.0 mm.*

*75. A method as claimed in claim 71, wherein the cartilage pieces are formed by freezing allograft cartilage with liquid nitrogen and milling the frozen cartilage.*

*76. A method as claimed in claim 71, wherein the cartilage pieces are formed by freeze-milling allograft cartilage subsequent to lyophilization of the allograft cartilage.*

*77. A method as claimed in claim 71, wherein the defect site includes a defect in articular cartilage.*

*78. A method as claimed in claim 77, wherein the cartilage pieces have an ability to promote the growth of new articular cartilage in the articular cartilage defect.*

*79. A method as claimed in claim 71, wherein the lyophilized, freeze-milled allograft cartilage pieces consist essentially of articular cartilage.*

*80. A method as claimed in claim 71, wherein the lyophilized, freeze-milled allograft cartilage pieces lack cell viability.*

*81. A method as claimed in claim 71, comprising the further steps of harvesting a donor tissue consisting essentially of articular cartilage, lyophilizing said donor tissue, and freeze-milling said donor tissue.*

*82. A method as claimed in claim 71, comprising the further step of forming the lyophilized, freeze-milled allograft cartilage pieces by a process including the step of milling frozen allograft articular cartilage.*

*83. A method as claimed in claim 71, wherein the lyophilized, freeze-milled allograft cartilage pieces are free of added chondrocytes.*

* * * * *